(12) United States Patent
Nakazawa et al.

(10) Patent No.: US 10,702,192 B2
(45) Date of Patent: Jul. 7, 2020

(54) DYNAMIC ANALYSIS SYSTEM

(71) Applicant: Konica Minolta, Inc., Tokyo (JP)

(72) Inventors: Masayuki Nakazawa, Hachioji (JP); Keiko Itaya, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 131 days.

(21) Appl. No.: 15/620,190

(22) Filed: Jun. 12, 2017

(65) Prior Publication Data

US 2017/0367623 A1 Dec. 28, 2017

(30) Foreign Application Priority Data

Jun. 28, 2016 (JP) ................................ 2016-127140

(51) Int. Cl.
*A61B 5/11* (2006.01)
*A61B 6/00* (2006.01)
*A61B 5/113* (2006.01)

(52) U.S. Cl.
CPC ............ *A61B 5/1128* (2013.01); *A61B 6/486* (2013.01); *A61B 6/50* (2013.01); *A61B 6/5217* (2013.01); *A61B 5/113* (2013.01)

(58) Field of Classification Search
CPC ...... A61N 2/006; A61N 1/3601; A61N 2/008; A61N 1/36025; A61N 1/36021; A61B 5/08; A61B 5/082; A61B 7/003; A61B 5/7264; A61B 5/055; A61B 7/026; A61B 8/00; A61B 2576/02; A61B 5/02028; A61B 5/0536; A61B 5/0813; A61B 6/032; A61B 8/13; A61B 5/411; A61B 6/5217; A61B 5/1128; A61B 5/113; A61B 6/486; A61B 6/50; A61B 5/087; A61B 6/463;
(Continued)

(56) References Cited

U.S. PATENT DOCUMENTS 6,790,183 B2 * 9/2004 Murphy .................. A61B 5/061
600/532
9,254,098 B2 * 2/2016 Charles .................. A61B 5/055
(Continued)

FOREIGN PATENT DOCUMENTS

JP 2009153678 A 7/2009
JP 2013192912 A 9/2013

OTHER PUBLICATIONS

JPO, Office Action for the corresponding Japanese patent application No. 2016-127140, dated Feb. 18, 2020, with English translation.
(Continued)

*Primary Examiner* — Aklilu K Woldemariam
(74) *Attorney, Agent, or Firm* — Lucas & Mercanti, LLP

(57) ABSTRACT

A dynamic analysis system includes: an analytic value calculation unit configured to calculate an analytic value in a plurality of time phases on the basis of a dynamic image in the plurality of time phases obtained by performing dynamic photography on the chest of a subject; a ventilation state calculation unit configured to calculate, using a non-linear function, an index value representing a ventilation state of a lung field from the analytic value in the plurality of time phases; a display unit; and a control unit configured to display the index value calculated on the plurality of time phases, on the display unit.

15 Claims, 17 Drawing Sheets

(58) Field of Classification Search
CPC ....... A61B 6/5288; A61B 6/541; A61B 5/061;
A61B 6/4233; A61B 6/507; A61B 6/54;
A61M 2230/40; A61M 2016/0036; A61M
2205/3375; A61M 2205/502; A61M
16/06; A61M 16/204; G01R 33/5601;
G01R 33/56308; G01R 33/56366; G06T
11/003; G06T 11/206; G06T 2207/10072;
G06T 2207/10081; G06T 2207/10116;
G06T 2207/10132; G06T 2207/30048;
G06T 2207/30061; G06T 2207/30104;
G06T 2211/40; G06T 7/0012; G06T
7/0016; G06T 7/30; G06T 2207/10016;
G06T 7/20; H04N 5/232; H04N 5/32
USPC ......... 382/128, 129, 131; 600/532, 533, 529
See application file for complete search history.

(56) References Cited

U.S. PATENT DOCUMENTS

| | | | | |
|---|---|---|---|---|
| 9,750,427 B2* | 9/2017 | Prisk | ...................... | A61B 5/055 |
| 2002/0183642 A1* | 12/2002 | Murphy | ................. | A61B 5/061 |
| | | | | 600/532 |
| 2002/0193700 A1* | 12/2002 | Bohm | ................. | A61B 5/0536 |
| | | | | 600/533 |
| 2004/0005273 A1* | 1/2004 | Driehuys | ............... | A61B 5/055 |
| | | | | 424/9.3 |
| 2007/0092864 A1* | 4/2007 | Reinhardt | ................. | G06T 7/11 |
| | | | | 435/4 |
| 2008/0281219 A1* | 11/2008 | Glickman | ........... | A61M 16/024 |
| | | | | 600/533 |
| 2010/0246925 A1* | 9/2010 | Nagatsuka | ............... | A61B 5/08 |
| | | | | 382/132 |
| 2010/0280358 A1* | 11/2010 | Mata | ...................... | A61B 5/055 |
| | | | | 600/420 |
| 2013/0002264 A1* | 1/2013 | Garber | ................. | A61B 5/0536 |
| | | | | 324/600 |
| 2013/0156158 A1* | 6/2013 | Noji | ......................... | A61B 5/08 |
| | | | | 378/62 |
| 2013/0331725 A1* | 12/2013 | Noji | ...................... | G06T 7/0016 |
| | | | | 600/534 |
| 2014/0155732 A1* | 6/2014 | Patz | ...................... | A61B 5/055 |
| | | | | 600/410 |
| 2015/0042677 A1* | 2/2015 | Shimamura | ............. | A61B 6/469 |
| | | | | 345/632 |
| 2015/0310625 A1* | 10/2015 | Shimamura | .......... | A61B 6/4233 |
| | | | | 382/132 |
| 2017/0025158 A1* | 1/2017 | Miyake | .................... | H04N 9/87 |

OTHER PUBLICATIONS

JPO, Office Action for the corresponding Japanese patent application No. 2016-127140, dated Apr. 28, 2020, with English translation,

* cited by examiner

DYNAMIC ANALYSIS SYSTEM

The entire disclosure of Japanese Patent Application No. 2016-127140 filed on Jun. 28, 2016 including description, claims, drawings, and abstract are incorporated herein by reference in its entirety.

BACKGROUND OF THE INVENTION

Field of the Invention

The present invention relates to a dynamic analysis system.

Description of the Related Art

There is a known art disclosed as an apparatus that performs image analysis on an X-ray dynamic image, or the like, and that provides information effective in the diagnosis of a lung ventilatory function. For example, JP 2009-153678 A describes a dynamic analysis system that obtains information on an absolute ventilation amount between a maximum expiration level and a maximum inspiration level, that calculates an estimated ventilation amount for a unit signal change amount on the basis of the absolute ventilation amount and the change amount of the signal value between the frame images of the maximum expiration level and the frame image of the maximum inspiration level, among the dynamic images, and calculates and supplies the estimated ventilation amount in each of the time phases by multiplying the value of estimated ventilation amount for the unit signal change amount, with the signal value change amount from the maximum expiration level or the maximum inspiration level in each of the time phases.

The technique disclosed in JP2009-153678A is based on the premise that there is a linear relationship between the signal value change amount and the estimated ventilation amount. In a case, however, where the ventilation amount is calculated using a linear function on the basis of the value obtained from a dynamic image, obtained information on the ventilation amount includes an error.

SUMMARY OF THE INVENTION

An object of the present invention is to be able to provide more accurate information on a ventilation state of a lung field.

To achieve the abovementioned object, according to an aspect, a dynamic analysis system reflecting one aspect of the present invention comprises:

an analytic value calculation unit configured to calculate an analytic value in a plurality of time phases on the basis of a dynamic image in the plurality of time phases obtained by performing dynamic photography on the chest of a subject;

a ventilation state calculation unit configured to calculate, using a non-linear function, an index value representing a ventilation state of a lung field from the analytic value in the plurality of time phases;

a display unit; and a control unit configured to display the index value calculated on the plurality of time phases, on the display unit.

According to an invention of Item. 2, in the dynamic analysis system of Item. 1, the analytic value is preferably one of transmitted X-ray intensity and a value calculated using the transmitted X-ray intensity.

According to an invention of Item. 3, in the dynamic analysis system of Item. 1 or 2, the index value is preferably a value representing one of an air amount within the lung field and a change amount of the air within the lung field.

According to an invention of Item. 4, in the dynamic analysis system of any one of Items. 1 to 3, the ventilation state calculation unit preferably calculates the index value from the analytic value using different functions for each of an expiratory phase and an inspiratory phase.

According to an invention of Item. 5, in the dynamic analysis system of Item. 4, the ventilation state calculation unit preferably uses a function in which an increase/decrease of the index value is reversed with respect to the increase/decrease of the analytic value, between the expiratory phase and the inspiratory phase.

According to an invention of Item. 6, in the dynamic analysis system of any one of Items. 1 to 5, the non-linear function is preferably a function having a downward curve at least in a portion of a region.

According to an invention of Item. 7, in the dynamic analysis system of Item. 6, the analytic value is preferably one of transmitted X-ray intensity and a value calculated using the transmitted X-ray intensity, the index value is preferably a value representing one of an air amount within the lung field and a change amount of air within the lung field, and the non-linear function used in the inspiratory phase is preferably a function having a downward curve at least in a portion of the region.

According to an invention of Item. 8, in the dynamic analysis system of any one of Items. 1 to 5, the non-linear function is preferably a function having an upward curve at least in a portion of a region.

According to an invention of Item. 9, in the dynamic analysis system of Item. 8, the analytic value is preferably one of transmitted X-ray intensity and a value calculated using the transmitted X-ray intensity, the index value is preferably a value representing one of an air amount within the lung field and a change amount of air within the lung field, and the non-linear function used in the expiratory phase is preferably a function having an upward curve at least in a portion of the region.

According to an invention of Item. 10, in the dynamic analysis system of any one of Items. 1 to 5, the non-linear function preferably includes a region having a downward curve and a region having an upward curve.

According to an invention of Item. 11, in the dynamic analysis system of Item. 10, the analytic value is preferably one of transmitted X-ray intensity and a value calculated using the transmitted X-ray intensity, the index value is preferably a value representing one of an air amount within the lung field and a change amount of air within the lung field, and the non-linear function used in the expiratory phase preferably includes a region having a downward curve and a region having an upward curve.

According to an invention of Item. 12, in the dynamic analysis system of anyone of Items. 1 to 11, the dynamic analysis system preferably further comprises:

a storage unit configured to store the non-linear function; and an information acquisition unit configured to obtain the non-linear function stored in the storage unit, wherein the ventilation state calculation unit preferably calculates the index value representing the ventilation state from the analytic value using the non-linear function obtained by the information acquisition unit.

According to an invention of Item. 13, in the dynamic analysis system of any one of Items. 1 to 11, the analytic value calculation unit preferably divides a lung field region included in the dynamic image in the plurality of time phases, into a plurality of regions, and calculates an analytic value of each of the divided regions in the plurality of time phases, the ventilation state calculation unit preferably calculates an index value representing a ventilation state of each of the regions from the analytic value of each of the regions in the plurality of time phases, and the control unit preferably displays the index value calculated for each of the regions in the plurality of time phases, on the display unit.

According to an invention of Item. 14, in the dynamic analysis system of Item. 13, the ventilation state calculation unit preferably calculates the index value representing the ventilation state of each of the regions from the analytic value of each of the regions, using different functions each of which corresponds to each of the regions.

According to an invention of Item. 15, in the dynamic analysis system of Item. 14, the dynamic analysis system preferably further comprises:

a storage unit configured to store different functions each of which corresponds to each of the regions; and an information acquisition unit configured to obtain the different functions each of which corresponds to each of the regions, from the storage unit, wherein the ventilation state calculation unit preferably calculates the index value representing the ventilation state of each of the regions using the different functions each of which corresponds to each of the regions obtained by the information acquisition unit.

According to an invention of Item. 16, in the dynamic analysis system of any one of Items. 1 to 15, the control unit preferably generates a schematic image representing the index value calculated on each of the dynamic images in the plurality of time phases, and displays the schematic image on the display unit by continuously switching the schematic image in accordance with the time phase.

According to an invention of Item. 17, in the dynamic analysis system of anyone of Items. 1 to 16, the dynamic analysis system preferably further comprises a photography unit configured to generate a dynamic image in a plurality of time phases by performing dynamic photography on the chest of a subject.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

Hereinafter, an embodiment of the present invention will be described in detail with reference to the drawings. However, the scope of the invention is not limited to the illustrated examples.

First, the configuration will be described.

Figure 1:
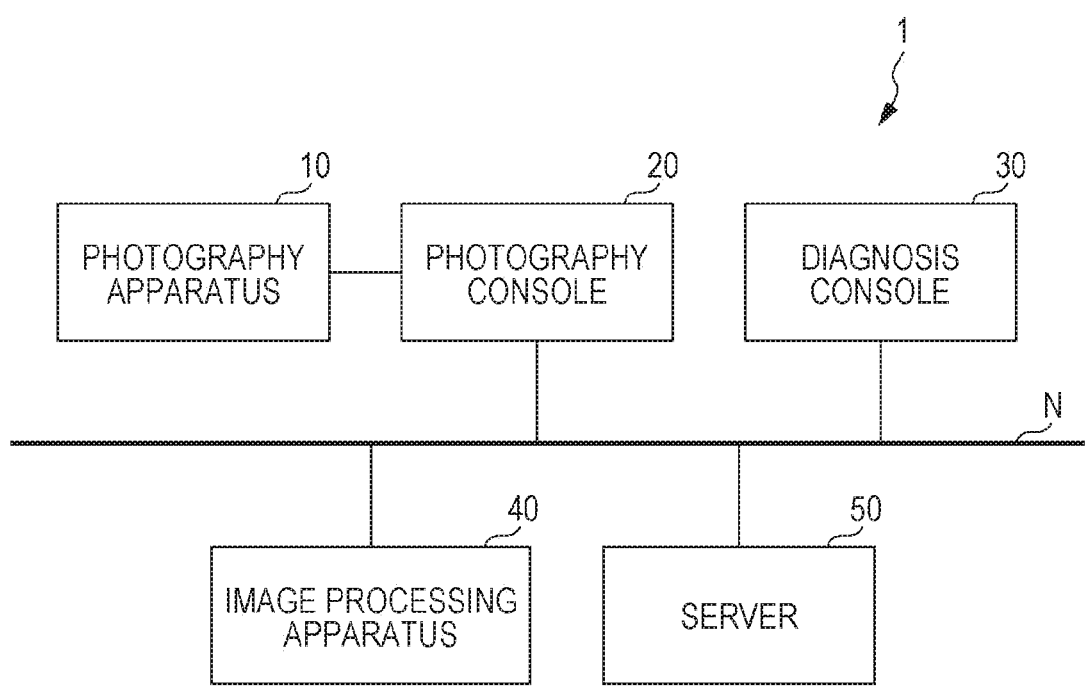
FIG. 1 is a diagram illustrating a dynamic analysis system in the present embodiment.

FIG. 1 illustrates a dynamic analysis system 1 in the present embodiment.

As illustrated in FIG. 1, the dynamic analysis system 1 includes a photography apparatus 10, a photography console 20, a diagnosis console 30, an image processing apparatus 40, and a server 50. The photography apparatus 10 and the photography console 20 are connected with each other via a communication cable, or the like. The photography console 20, the diagnosis console 30, the image processing apparatus 40, and the server 50 are connected with each other via a communication network N such as a local area network (LAN).

Figure 2:
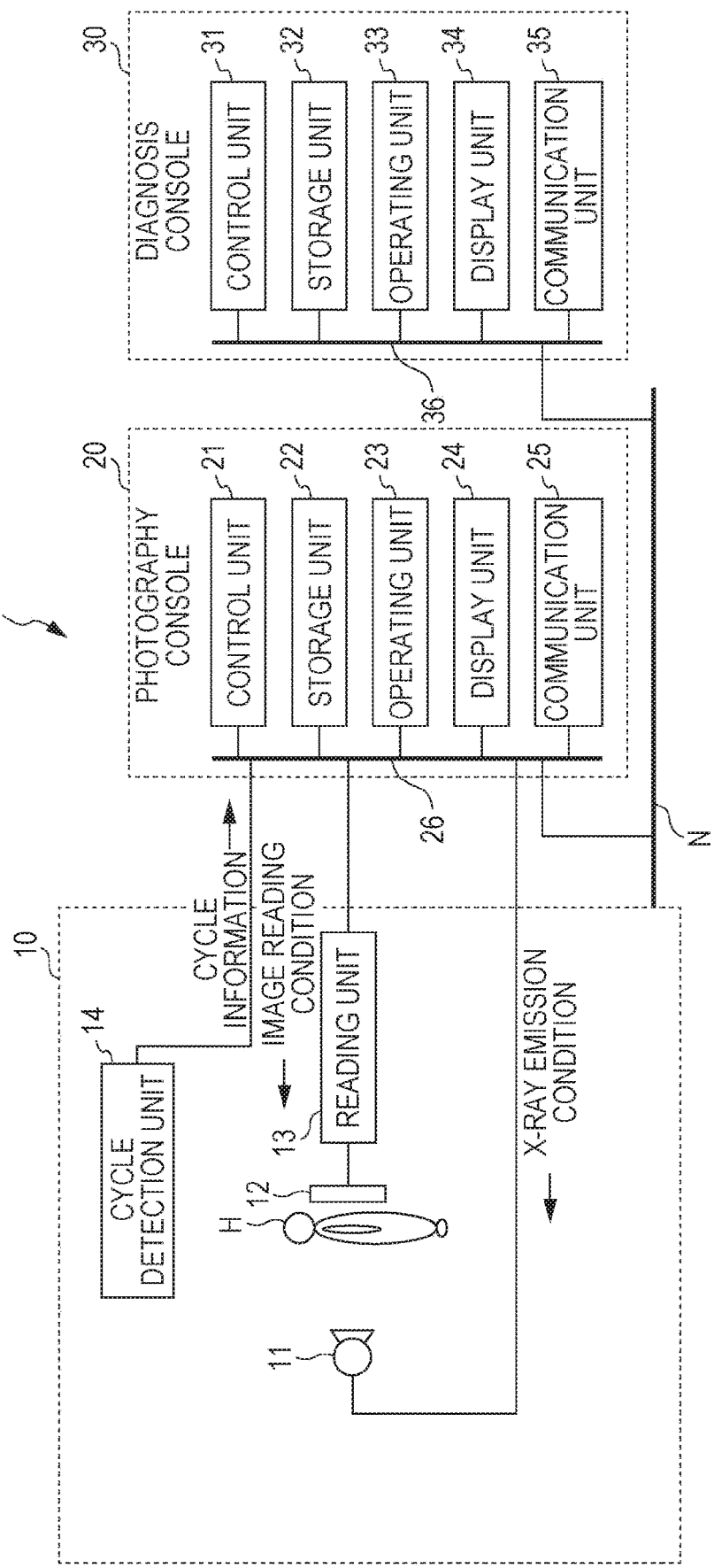
FIG. 2 is a diagram illustrating a functional configuration of a photography apparatus, a photography console, and a diagnosis console in FIG. 1.

The photography apparatus 10, the photography console 20, and the diagnosis console 30 will be described in more detail with reference to FIG. 2. The photography apparatus 10 includes an X-ray source 11, a detector 12, a reading unit 13, and a cycle detection unit 14. In contrast, the photography console 20 includes a control unit 21, a storage unit 22, an operating unit 23, a display unit 24, and a communication unit 25. Similarly, the diagnosis console 30 includes a control unit 31, a storage unit 32, an operating unit 33, a display unit 34, and a communication unit 35.

First, the photography apparatus 10 will be described.

The photography apparatus 10 emits an X-ray to a subject H and reads an X-ray image from the detector 12. The photography apparatus 10 is capable of performing dynamic photography. The dynamic photography is a photography method of obtaining a dynamic image (frame image) in a plurality of time phases by performing photography continuously. The dynamic image is a photographed image obtained by dynamic photography. In the present embodiment, the dynamic image is an X-ray image.

The X-ray source 11 emits an X-ray in accordance with the control of the control unit 21 in the photography console 20. Exemplary X-ray emission conditions to be controlled include a pulse rate, pulse duration, pulse interval, emission start/finish timings, X-ray tube current, X-ray tube voltage, and a filter value, at the time of continuous photography in dynamic photography. The pulse rate is the number of photographing for a unit time. The pulse duration is X-ray emission time for a single photography. The pulse interval is a time from the starting of X-ray emission to the X-ray emission in the next photography, during continuous photography.

The detector 12 is arranged at a position opposite to the X-ray source 11 across the subject H. The detector 12 is a flat panel detector (FPD), on which X-ray detection sensors are arranged in a matrix. That is, an X-ray is converted into an electrical signal that corresponds to the intensity of the X-ray, and stored in each of pixels (detection sensors), whereby an X-ray image is stored in the detector 12.

The reading unit 13 performs processing of reading an X-ray image from the detector 12 and transmits the read X-ray image to the photography console 20. Note that the reading operation is controlled by the control unit 21. Exemplary image reading conditions to be controlled include a frame rate, a frame interval, and a pixel size. The frame rate, the frame interval are used synonymously with the above-described pulse rate and the pulse interval.

The cycle detection unit 14 detects a cycle of biological reaction for photography sites of the subject H. In a case, for example, where the photography site is a chest including the lung as in the present embodiment, a respiratory cycle is detected with application of a respiration monitoring belt, a CCD camera, an optical camera, and a spirometer.

The cycle detection unit 14 outputs detected cycle information to the control unit 21 of the photography console 20.

Next, the photography console 20 and the diagnosis console 30 will be described.

The photography console 20 is used for photography operation by a technician, specifically, for inputting photography conditions, etc. and for displaying an X-ray image from the photography apparatus 10 for technician's verification. The diagnosis console 30 is used for operation by a physician, specifically, for displaying an X-ray image transmitted from the photography console 20 for physician's verification.

The functions of components of the diagnosis console 30 (control unit 31, storage unit 32, operating unit 33, display unit 34, communication unit 35) are fundamentally the same as the functions of the components of the photography console 20 (control unit 21, storage unit 22, operating unit 23, display unit 24, communication unit 25). Accordingly, the components of the photography console 20 will be representatively described and description of the components the diagnosis console 30 will be omitted.

The control unit 21 includes a central processing unit (CPU) and a random access memory (RAM). The control unit 21 reads various programs stored in the storage unit 22 by the CPU, expands the program into the RAM, and executes processing by performing various calculations in cooperation with expanded programs, and by performing centralized control of operation on individual components.

Note that the control unit 21 has a timer function of clocking the time using a CPU clock.

The storage unit 22 is a memory such as a hard disk, and stores various programs used by the control unit 21 and parameters, etc. needed for execution of the programs. For example, the storage unit 22 stores photography conditions (X-ray emission condition, image reading condition for X-ray image, or the like) optimized for each of photography sites.

The operating unit 23 includes a keyboard and a mouse, generates an operation signal in accordance with operation thereof, and outputs the operation signal to the control unit 21.

The display unit 24 includes a display and displays various operation screens and X-ray images obtained by photography, etc. in accordance with display control of the control unit 21.

The communication unit 25 includes an interface for communication and performs communication with an external device connected to the network N.

Next, the image processing apparatus 40 and the server 50 will be described.

The image processing apparatus 40 and the server 50 are used for supplying the X-ray image obtained by photography.

Figure 3:
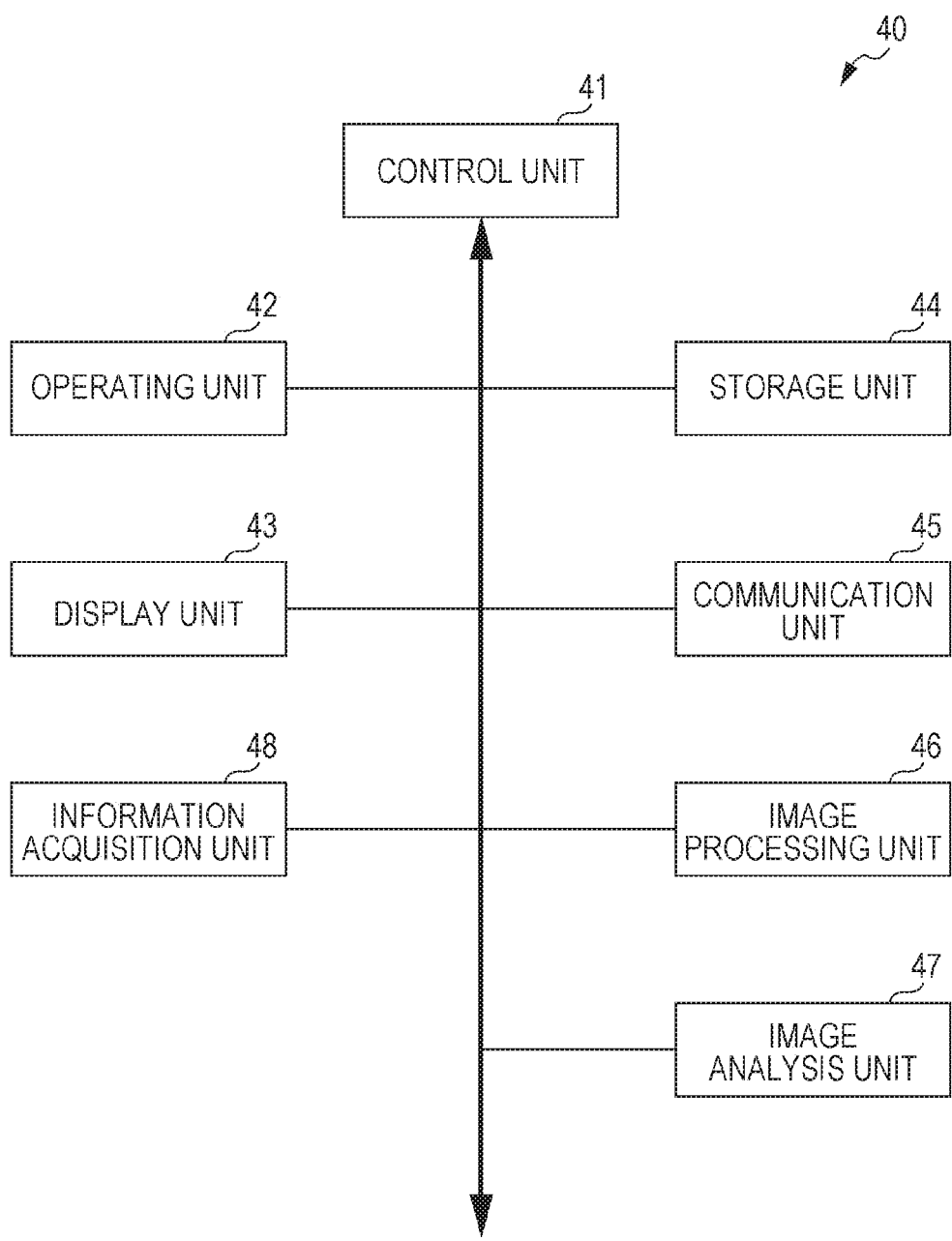
FIG. 3 is a diagram illustrating a functional configuration of an image processing apparatus in FIG. 1.

The image processing apparatus 40 will be described with reference to FIG. 3.

The image processing apparatus 40 performs image processing and image analysis on the X-ray image. As illustrated in FIG. 3, the image processing apparatus 40 includes a control unit 41, an operating unit 42, a display unit 43, a storage unit 44, a communication unit 45, an image processing unit 46, an image analysis unit 47, and an information acquisition unit 48.

Fundamental functions of the control unit 41 to the communication unit 45 are same as the fundamental functions of the above-described control unit 21 to the communication unit 25 of the photography console 20, and thus, detailed description therefore will be omitted. Note that the storage unit 44 stores a function for calculating an index value Y representing the ventilation state from an analytic value X is stored for each of regions divided in step S12 in FIG. 5.

The image processing unit 46 performs image processing such as tone conversion processing and frequency adjustment processing on an X-ray image. Image processing of the type corresponding to the photography site is performed under the image processing condition corresponding to the photography site.

The image analysis unit 47 analyzes a dynamic image in a plurality of time phases obtained by dynamic photography on the chest, and calculates the analytic value X in each of the time phases and the index value Y representing a ventilation state. That is, the image analysis unit 47 functions as an analytic value calculation unit and a ventilation state calculation unit. Specific calculation methods will be described below.

Figure 5:
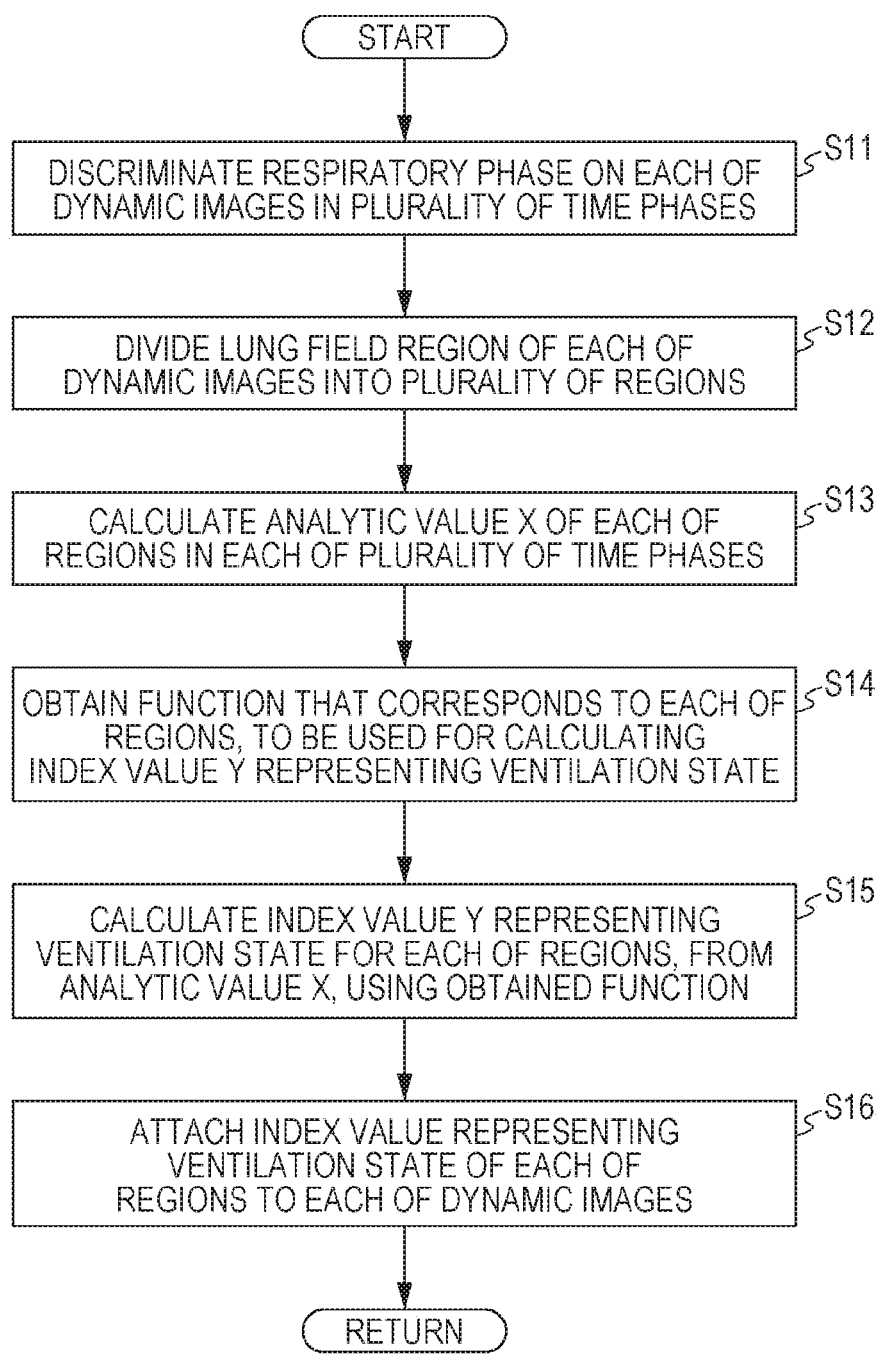
FIG. 5 is a diagram illustrating a flow of processing of calculating an index value representing a ventilation state.

The information acquisition unit 48 obtains a function that corresponds to each of the regions divided in step S12 in FIG. 5 by reading the function from the storage unit 44 and outputs the function to the image analysis unit 47.

The image processing unit 46, the image analysis unit 47, and the information acquisition unit 48 may be implemented by the control unit 41 in cooperation with the programs, or may be implemented by dedicated hardware.

The server 50 includes a large capacity memory and stores in this memory the X-ray image image-processed by the image processing apparatus 40, and manages the X-ray image. The X-ray image stored in the server 50 is distributed in response to a request from the diagnosis console 30 and provided for diagnosis.

Next, operation will be described.

The dynamic analysis system 1 according to the present embodiment performs dynamic photography on the chest and image analysis on an obtained dynamic image in a plurality of time phases, and calculates and displays the index value Y representing the ventilation state in each of the time phases.

Figure 4:
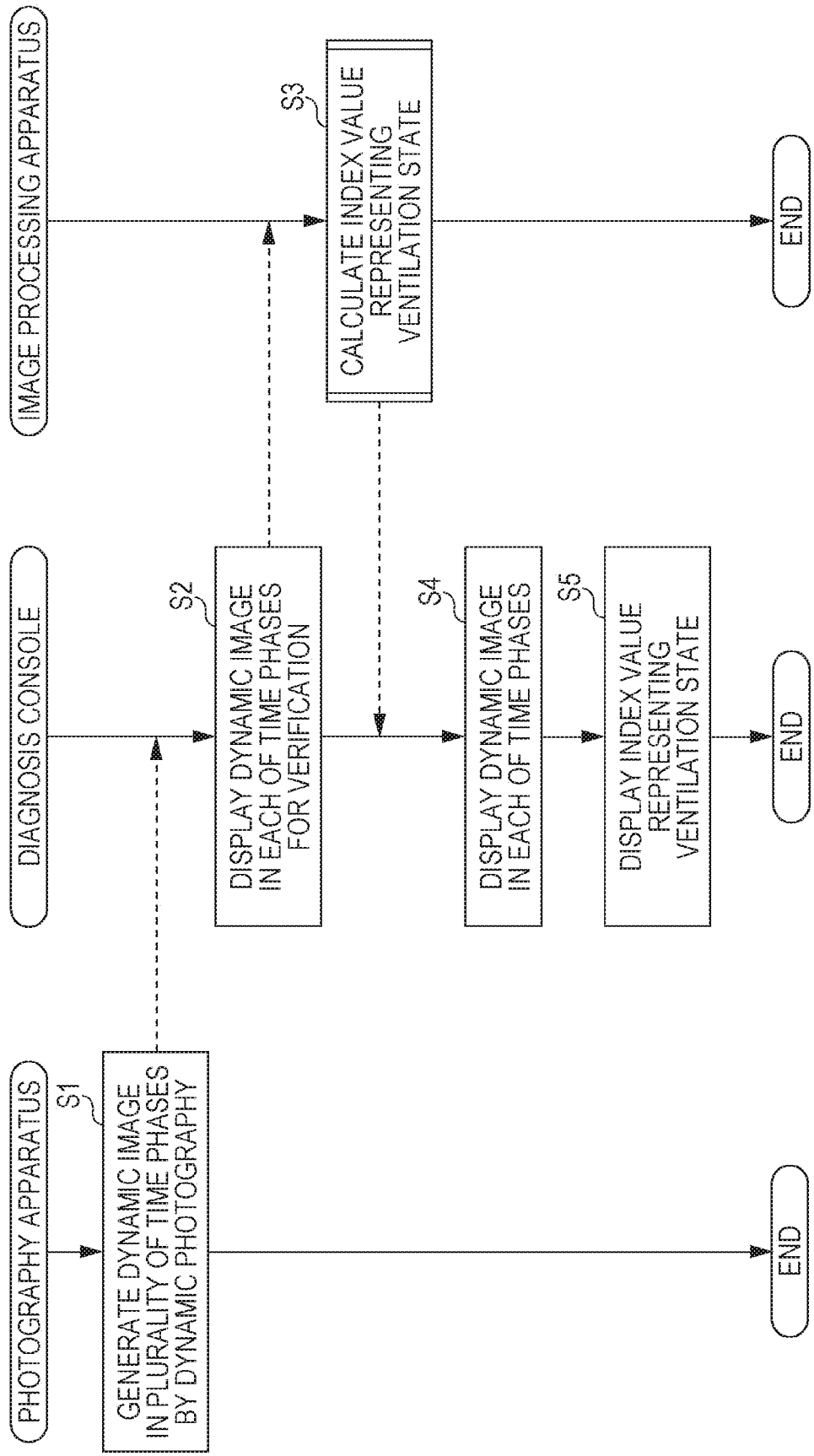
FIG. 4 is a diagram illustrating a flow of processing on the dynamic analysis system.

FIG. 4 is a flowchart illustrating a flow of processing on apparatuses that function mainly at this time, that is, the photography apparatus 10, the diagnosis console 30, and the image processing apparatus 40.

As illustrated in FIG. 4, dynamic photography is performed on the photography apparatus 10 and a dynamic image in a plurality of time phases is generated (step S1). The dynamic photography is performed so as to at least generate the dynamic image in the plurality of time phases for one respiratory phase.

In photography, via the operating unit 23 the photography console 20, a photography technician performs input of patient information on the subject H, designation operation, etc. regarding examination information (photography site, chest in this example), the analysis target type (e.g., ventilation, perfusion), the body position (e.g., standing position and recumbent position), or the like. The patient information includes information representing attributes of the patient such as age, sex, weight, height, in addition to the name of the subject H as the patient.

On the photography console 20, the control unit 21 reads the photography condition according to the designated photography site, from the storage unit 22, and sets the photography condition as an X-ray emission condition on the X-ray source 11 of the photography apparatus 10, and as an image reading condition on the reading unit 13. Hereinafter, description follows on the assumption that photography of the "chest (lung)" is designated as the photography site by the photography technician. In a case where the lung is photographed in order to check the ventilatory function, the average respiratory cycle is approximately 0.3 times/second. In consideration of this fact, in order to enable photography of a dynamic image in a plurality of time phases for at least one respiratory phase, the following photography condition would be set for example.

Frame rate (pulse rate): three frames/second (namely, three shots of photography per second)

Pixel size: 400 μm

Image size: 40 cm×30 cm

Tube voltage: 120 kV

Tube current: 50 mA

Photography timing: for every frame interval from the timing (photography start timing) of transition point from inspiration to expiration Note that the control unit 21 corrects conditions such as the frame rate on the basis of respiratory cycle information detected by the cycle detection unit 14. For example, the control unit 21 calculates the frame rate and re-sets the frame rate such that one respiratory phase can be photographed with the predetermined number of frames (e.g. 10 frames) on the basis of the detected respiratory cycle. In the above-described exemplary frame rate condition, in a case where the respiratory cycle detected by the cycle detection unit 14 is 0.25 times/second, the frame rate would be corrected to 2.5 frames/second.

After photography condition setting is completed, the control unit 21 determines whether it is a photography start timing, that is, whether it is a timing where one respiratory phase starts (e.g. transition point from inspiration to expiration) on the basis of the respiratory cycle information detected by the cycle detection unit 14. When this is the photography start timing, the control unit 21 starts dynamic photography by controlling the X-ray source 11 and the reading unit 13. Moreover, the control unit 21 clocks photography time needed from start to finish of the photography in accordance with the start of the dynamic photography.

The photography apparatus 10 emits an X-ray with a predetermined pulse rate in accordance with the X-ray emission condition that has been set. Similarly, the reading unit 13 performs reading processing of the X-ray image with the predetermine frame rate from the detector 12 in accordance with the image reading condition that has been set. Synchronization of the X-ray emission operation with the image reading operation is performed by the control unit 21. With this process, a dynamic image in the plurality of time phases is generated and output to the photography console 20.

Note that in the present embodiment, dynamic photography of the subject H is performed from the front and side of the chest.

The photography console 20 displays the dynamic image in each of time phases, obtained by dynamic photography with the display control of the control unit 21, on the display unit 24. This display is for enabling the photography technician to verify image quality, or the like. After verification operation of the photography technician via the operating unit 23, the control unit 21 attaches, onto the dynamic image in each of the time phases, an ID for identification of a series of photography, a number indicating the order of photography, patient information, examination information, photography time information, or the like, and transmits the dynamic image with the attached information to the diagnosis console 30. The diagnosis console 30 also performs display for verification in a similar manner (step S2). After verification operation, the dynamic image in each of the time phases is transmitted to the image processing apparatus 40.

The image processing apparatus 40 causes the image processing unit 46 to perform image processing on the dynamic image in each of the time phases according to the photography site (herein, the chest), and thereafter, causes the image analysis unit 47 to calculate the index value Y representing the ventilation state regarding the dynamic image in each of the time phases (step S3).

The processing of calculating the index value Y representing the ventilation state will be described with reference to FIG. 5.

Figure 6:
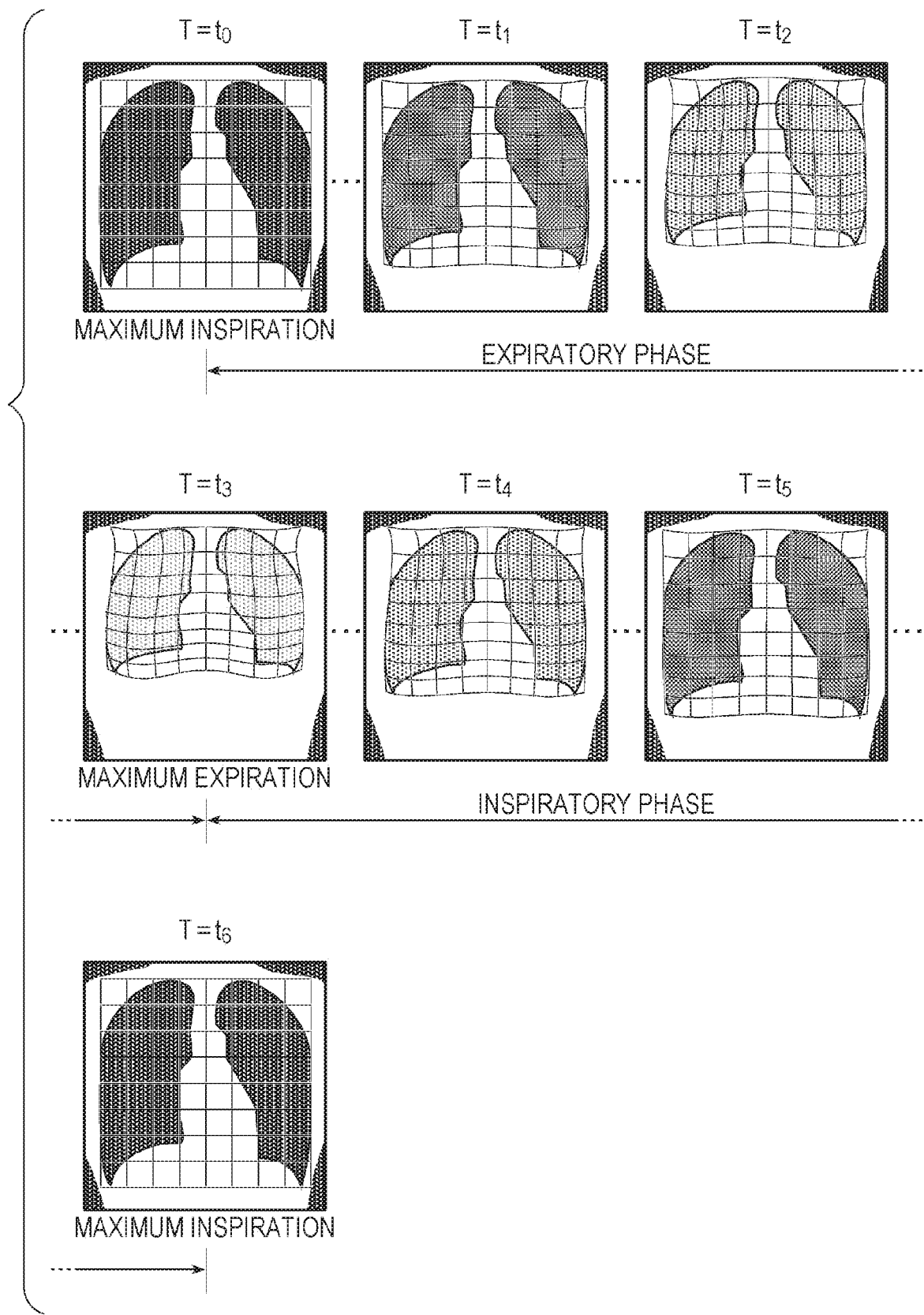
FIG. 6 is a diagram illustrating a dynamic image in a plurality of time phases.

As illustrated in FIG. 5, the image analysis unit 47 initially discriminates the respiratory phase regarding each of the dynamic images in the plurality of time phases (step S11). The lower lung contracts during expiration and expands during inspiration. Accordingly, the image analysis unit 47 calculates the area (number of pixels) of the lung field region on the dynamic image associated with each of the time phases, and discriminates the dynamic image in a rage from the time phase having the maximum area to the time phase having the minimum area, as the expiratory phase, and discriminates the dynamic image in a range from the time phase having the minimum area to the time phase having the maximum area, as the inspiratory phase. FIG. 6 illustrates a result of discriminating the respiratory phase regarding the dynamic image in each of time phases T (T=$t_0$ to $t_6$).

Any method may be applied to the recognition of the lung field region. For example, a threshold is obtained by discriminant analysis from a signal value histogram of a standard image and a region with a signal higher than the threshold may be primarily detected as the lung field region. Next, edge detection is performed near a boundary of the primarily detected region, and points along the boundary to achieve the maximum edge is extracted from the small region near the boundary, thereby enabling detection of the boundary of the lung field region.

Next, the image analysis unit 47 divides the lung field region on each of the dynamic images into a plurality of regions (step S12).

Figure 7A:
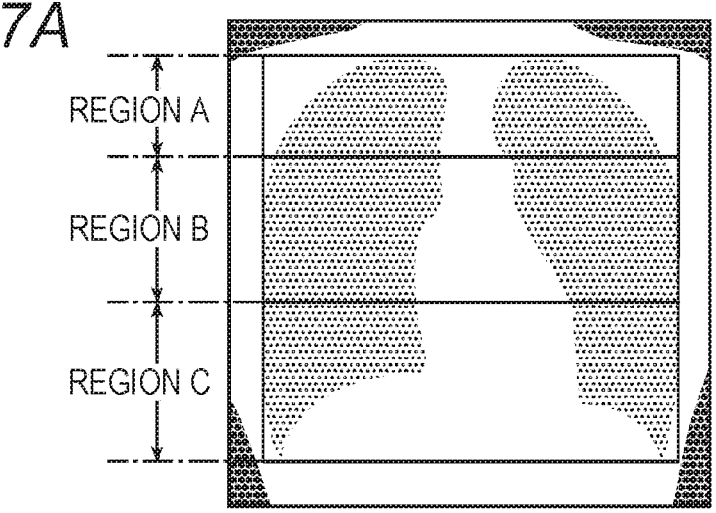
FIGS. 7A to 7C are diagrams each illustrating a dividing example of a region.
Figure 7B:
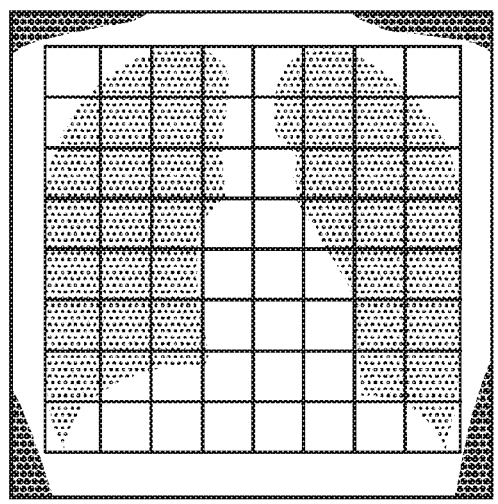

In the present embodiment, the lung field region is vertically divided into three regions (regions A, B, and C from the top) as illustrated in FIG. 7A. This is in consideration of the difference in an absolute ventilation amount between the upper lung field and the lower lung field due to the difference in the lung field volume. This is also in consideration of the difference in the force applied to the alveoli between the upper lung field and the lower lung field due to the gravity in case of the standing position state, which leads to the difference in a delay level of a change of the air amount within the lung field with respect to the volume change with the respiratory motion of the lung field (details will be described below). As illustrated in FIG. 7B, the lung field region may be divided into a plurality of small regions (for example, squares of 0.4 cm to 4 cm).

Association of each of the divided regions between the dynamic images in the plurality of time phases can be performed by local matching. Local matching is a technique of first defining a certain dynamic image as a standard image and dividing this standard image into regions, and then, associating each of the divided regions with a region in another dynamic image having a high matching level. The matching level is a degree of consistency between images, obtainable with the least square method and cross-correlation.

Figure 7C:
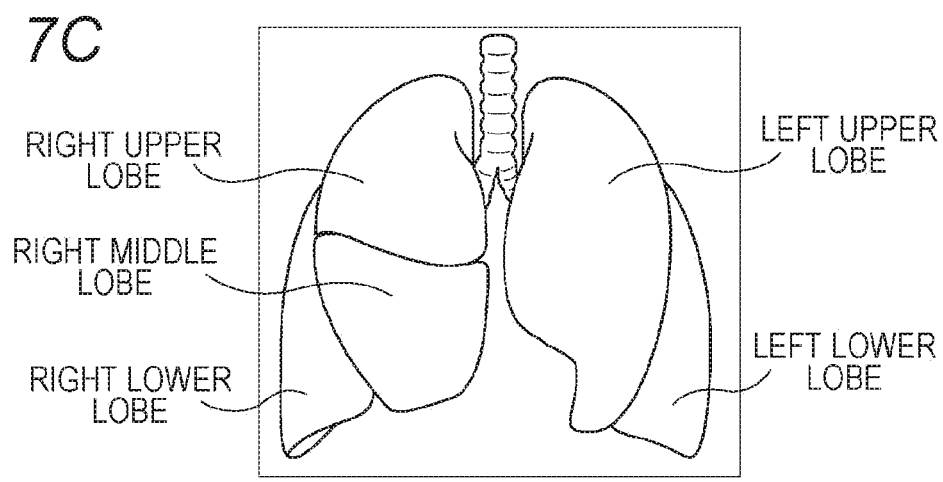

As illustrated in FIG. 7C, it is also allowable to divide the lung field region into the right upper lobe and the left upper lobe, in accordance with the anatomical structure of the lung. In this case, it is possible to grasp the ventilation state in accordance with the anatomical structure. The division may be performed after recognition of individual regions of anatomical structures using a reference image in which anatomical structural positions and names are predetermined, by performing image conversion using non-linear warping, or the like, such that the lung field region of the reference image and the lung field region on each of the dynamic images may substantially be aligned.

While the region divided in step S12 in the present embodiment includes a plurality of pixels, it is allowable to include a single pixel.

Next, the image analysis unit 47 calculates the analytic value X for each of regions in each of the plurality of time phases (step S13).

The analytic value X is not particularly limited as long as it is, for example, a signal value within each of the divided region or a value calculated on the basis of the signal value, and the value representing X-ray transmittance state within the region.

Herein, the signal value is a value of each of the pixels (pixel signal value) of the dynamic image. The intensity of the X-ray that has transmitted through the subject (transmitted X-ray intensity) can be used as the signal value. This may be value in a unit of the transmitted X-ray intensity, for example, values in mR and mGy, or may be a value converted into a numerical value having a linear relationship with these values. For example, it is possible to use the value obtained from allocating the transmitted X-ray intensity in a range 0 mR to 1000 mR, onto the 12-bit integers (0 to 4095), as a signal value. It is also possible to use, as the signal value, the value obtained by conversion from the transmitted X-ray intensity or the value having linear relationship with the intensity using a predetermined function. For example, it is possible to perform logarithmic transformation on the transmitted X-ray intensity and use this transformed value as the signal value. Moreover, while the present embodiment describes a case where the signal value increases together with the increase in the transmitted X-ray intensity, it is possible to configure such that the signal value decreases together with the increase in the transmitted X-ray intensity. For example, it is possible to use the value obtained from allocating the transmitted X-ray intensity in a range 0 mR to 1000 mR, onto 4095 to 0, as the signal value.

For example, the analytic value X may be calculated such that a histogram of the signal value is calculated first for each of the regions, and the total sum obtained by multiplying the frequency with the signal value that corresponds to the lung field may be calculated as the analytic value X. It is also allowable to calculate the value as a representative value of the signal value within the region, for example, the mean, median, and the mode value, as the analytic value X. The mean value may be an arithmetic mean or a weighted mean. It is also allowable to use a value obtained by filtering the calculated representative value with a low pass filter in the time direction, as the analytic value X. Moreover, the analytic value X may be a calculated value itself, or a relative value (e.g. difference or ratio) between the analytic value calculated for each of the frames (dynamic image) and the analytic value calculated for a predetermined frame.

Alternatively, the analytic value X may be a value calculated on the basis of the number of pixels within each of the divided regions.

In the present embodiment, the analytic value X that corresponds to the volume of each of the regions, calculated on the basis of the number of pixels of each of the regions, illustrated in the following (Formula 1) is calculated.

$$X = M \times b \quad \text{(Formula 1)}$$

where, M is the area of each of the regions divided from the lung field region on the dynamic image photographed from the front, and b is a thickness of the lung of each of the regions divided on the dynamic image photographed from the side. The area M can be obtained, for example, by counting the number of pixels of each of the regions (lung field region) divided on the dynamic image photographed from the front.

Next, the information acquisition unit 48 obtains a function according to each of the divided regions, to be used for calculating the index value Y representing the ventilation state, stored in the storage unit 44 (step S14).

In the present embodiment, the storage unit 44 stores functions that differ in accordance with each of the regions divided in step S12. The "functions that differ in accordance with each of the regions" means there are mutually different functions in at least some of the divided regions, and thus, there is no need to have functions to be mutually different in all the regions. In the present embodiment, the information acquisition unit 48 reads the function according to each of the regions divided in step S12 from the storage unit 44. Alternatively, it is also allowable to configure such that the server 50 stores the function according to each of the regions, and that the information acquisition unit 48 obtains the function from the server 50.

The horizontal axis represents the analytic value X and the vertical axis represents the index value Y representing the ventilation state. When the analytic value X at the maximum expiration level is defined as X1, and the analytic value X at the maximum inspiration level is defined as X2, while the index value Y representing the ventilation state at the maximum expiration level is defined as Y1 and the index value Y representing the ventilation state at the maximum inspiration level is defined as Y2, the function obtained in step S14 is a function to be used at the time of calculating the index value Y between the index values Y1 and the Y2 from the analytic value X between the analytic values X1 and X2 (refer to FIG. 13). While the range X1 to X2, and the range Y1 to Y2 can be determined on the basis of the relationship between representative analytic value and representative index value of a healthy subject, it is not limited to the determined values.

The index value Y representing the ventilation state is a value representing the air amount within each of the regions divided in the lung field region or the change amount of the air within each of the divided regions (ventilation amount).

Now, the relationship between the air amount and the ventilation amount will be described with reference to FIGS. 8A to 8C.

Figure 8A:
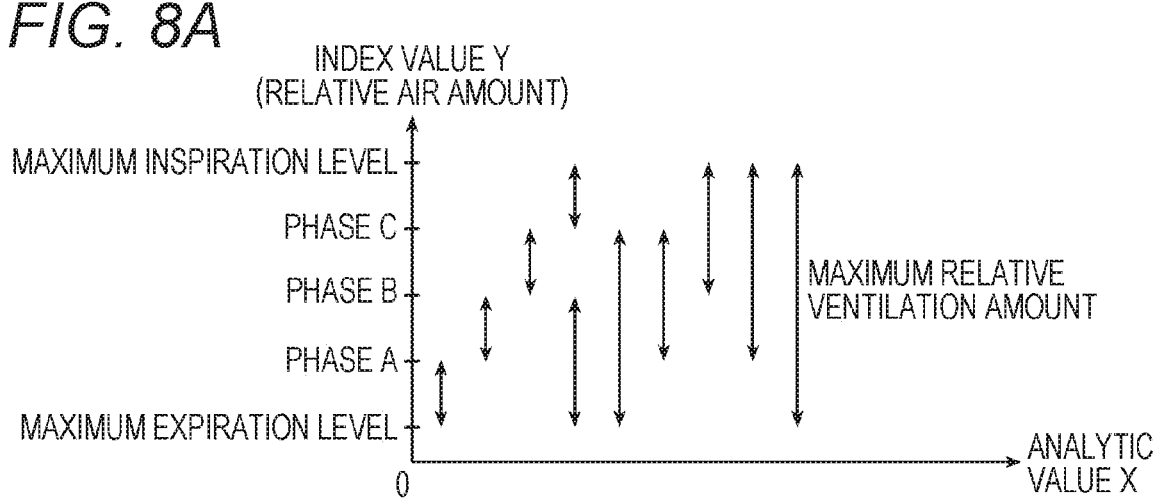
FIGS. 8A to 8C are diagrams each illustrating a relationship between the air amount and the ventilation amount.
Figure 8B:
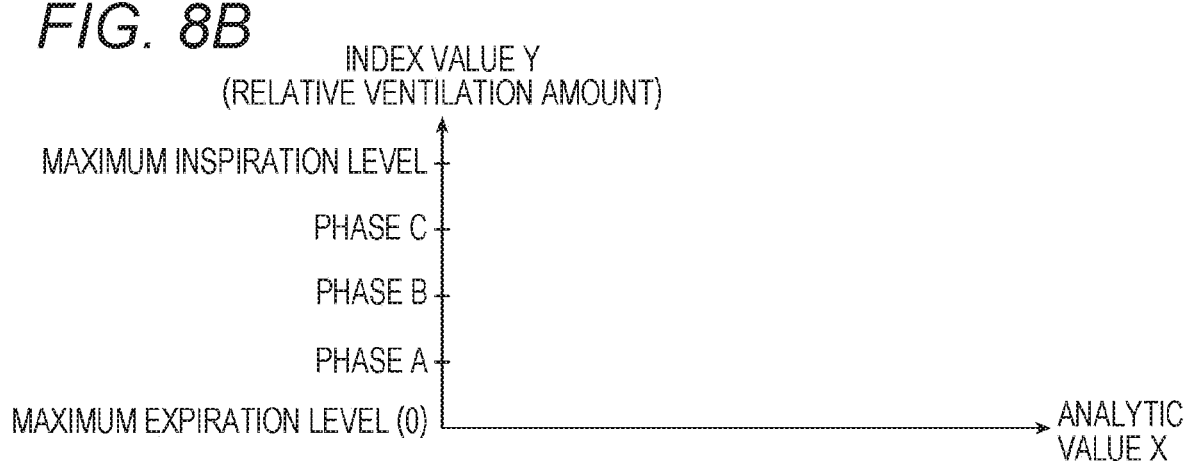
Figure 8C:
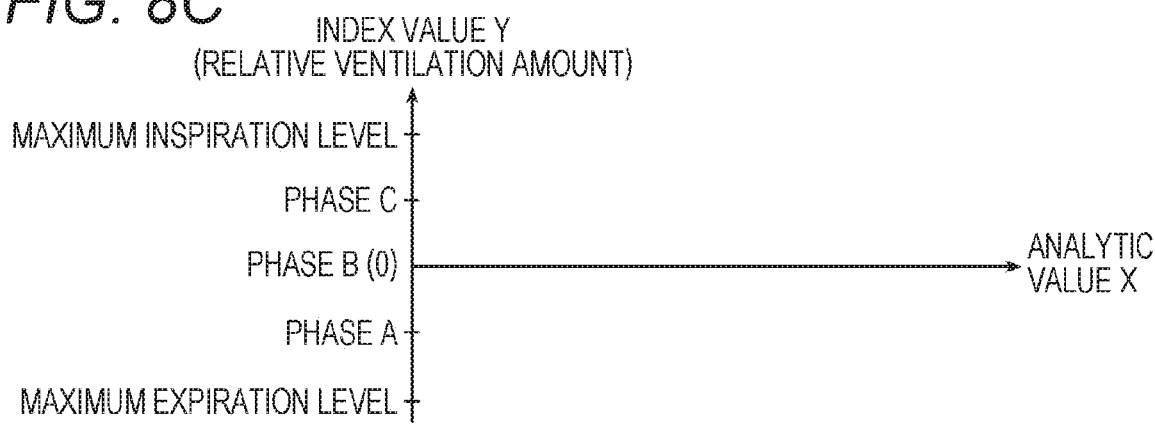

FIG. 8A illustrates graph axes representing the relationship between the two amounts in a case where the horizontal axis represents the analytic value X while the index value Y on the vertical axis represents the air amount. The air amount is the amount of air within the lung field region (within each of the divided regions), while the ventilation amount is a difference in the air amount (air change amount) between a certain phase and another phase of the respiratory cycle. Specifically, the amount indicated by arrows in FIG. 8A corresponds to the ventilation amount. For example, in a case where the change amount of air from the air amount at the maximum expiration level is defined as the ventilation amount, the graph is obtained as a graph in which the origin (0) of the air amount on the vertical axis in FIG. 8A is shifted to the maximum expiration level, as illustrated in FIG. 8B. For example, in a case where the change amount of air from the air amount at an intermediate phase B is defined as the ventilation amount, the graph is obtained as a graph in which the origin (0) of the air amount on the vertical axis in FIG. 8A is shifted to the phase B, as illustrated in FIG. 8C. That is, the function form indicating the analytic value X and the function form indicating the index value Y are the same between the case where the vertical axis represents the air amount and the case where the vertical axis represents the ventilation amount.

While the following describes the case where the vertical axis, that is, the index value Y representing the ventilation state corresponds to the ventilation amount (relative ventilation amount), the description can be applied similarly to the case where the vertical axis corresponds to the air amount (relative air amount). The relative ventilation amount is a numerical value relatively representing the magnitude of the ventilation amount in all the lung field or in a predetermined region within the lung field. The value can be a real number ranging from 0 to 1, or a 2-bit integer value from 0 to 4095, for example.

Now the relationship between the alveolar volume and the internal pressure during respiration, and the relationship between the internal pressure and air flow during respiration will be described.

Figure 9:
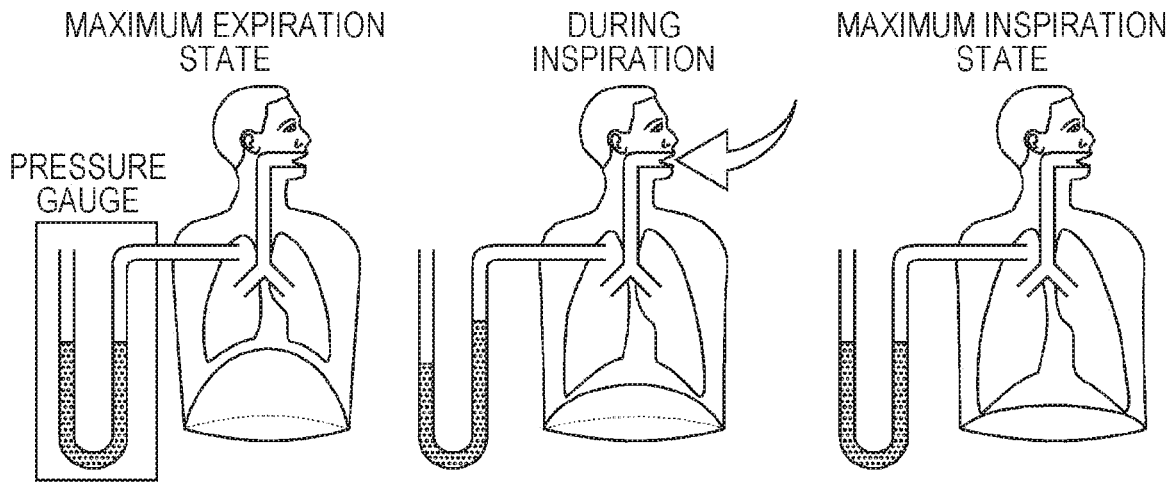
FIG. 9 is a diagram illustrating a relationship between the alveolar volume and an internal pressure during inspiration, and relationship between the internal pressure and air flow during inspiration.

FIG. 9 is a diagram illustrating a relationship between the alveolar volume and an internal pressure during inspiration, and relationship between the internal pressure and air flow during inspiration. As illustrated in FIG. 9, the pressure inside the alveoli is at atmospheric pressure with no air movement (ventilation) in the maximum expiration state. During inspiration, inspiratory muscles (mainly diaphragm and external intercostal muscles) contract to expand the chest, leading to expanded lung (alveoli) and increased lung volume. With the increase in the lung volume, the pressure inside the alveoli is lowered below atmospheric pressure, and inspiration begins later than the increase in the volume. On completion of contraction of the inspiratory muscles, the increase in the alveolar volume stops. When the inflow of the air catches up with the increase in the lung volume, the pressure inside the alveoli is equalized with the atmospheric pressure, thereby stopping inspiration.

Figure 10:
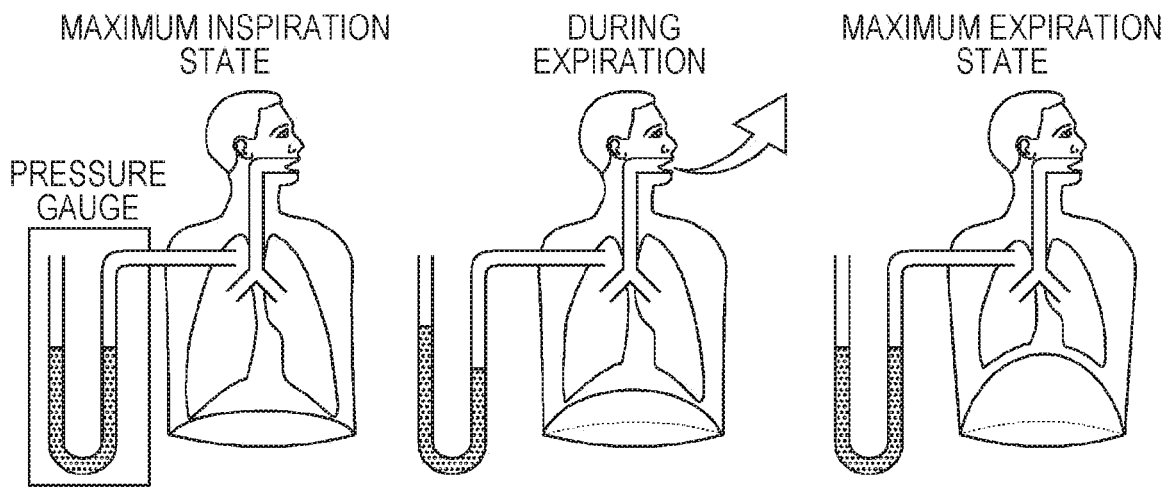
FIG. 10 is a diagram illustrating a relationship during expiration, between the alveolar volume and an internal pressure, and between the internal pressure and air flow.

FIG. 10 is a diagram illustrating a relationship during expiration, between the alveolar volume and an internal pressure, and between the internal pressure and air flow. As illustrated in FIG. 10, the pressure inside the alveoli is at atmospheric pressure with no air movement (ventilation) in the maximum inspiration state. During expiration, expiratory muscles (mainly abdominal muscles and internal intercostal muscles) contract to compress the chest, leading to the compressed lung (alveoli) and reduced lung volume. With the reduction of the lung volume, the pressure inside the alveoli is increased above atmospheric pressure, and expiration begins later than the reduction of the volume. On completion of contraction of the expiratory muscles, the compression of the alveoli stops. When the outflow of the air catches up with the reduction of the lung volume, the pressure inside the alveoli is equalized with the atmospheric pressure, thereby stopping expiration.

Figure 11:
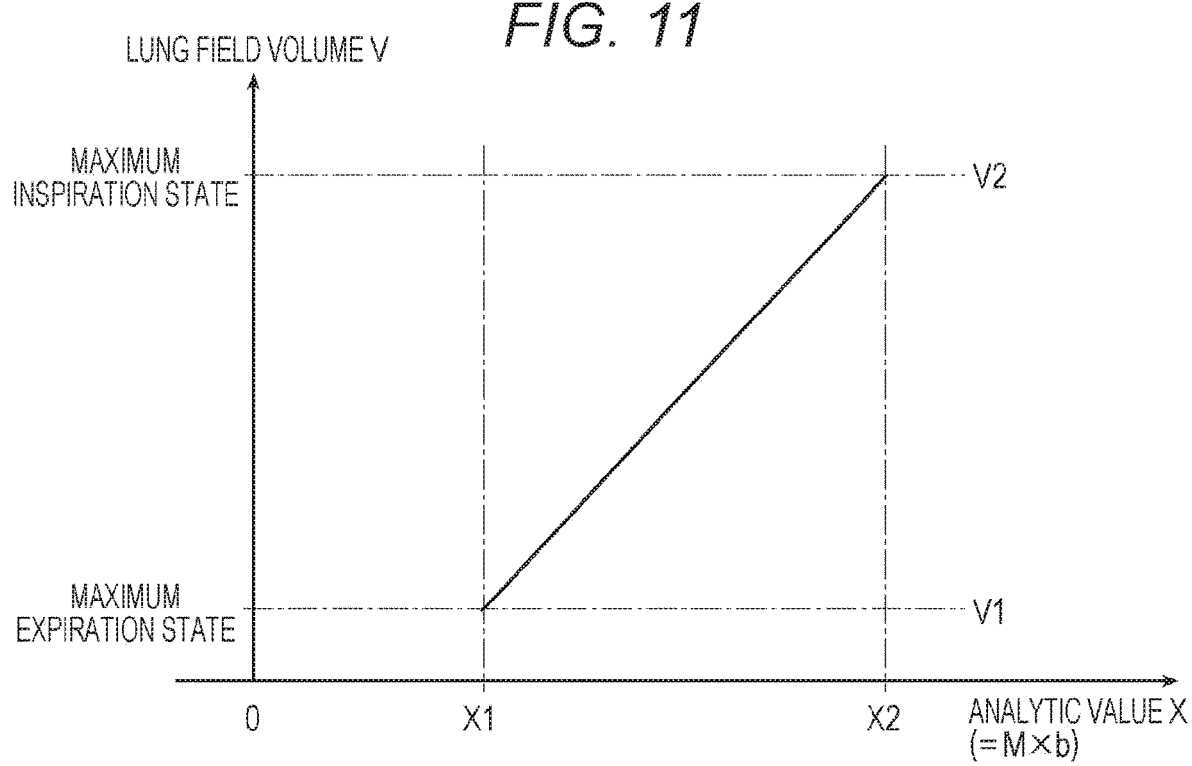
FIG. 11 is a diagram illustrating a relationship between an analytic value (M×b) and a lung field volume.
Figure 12:
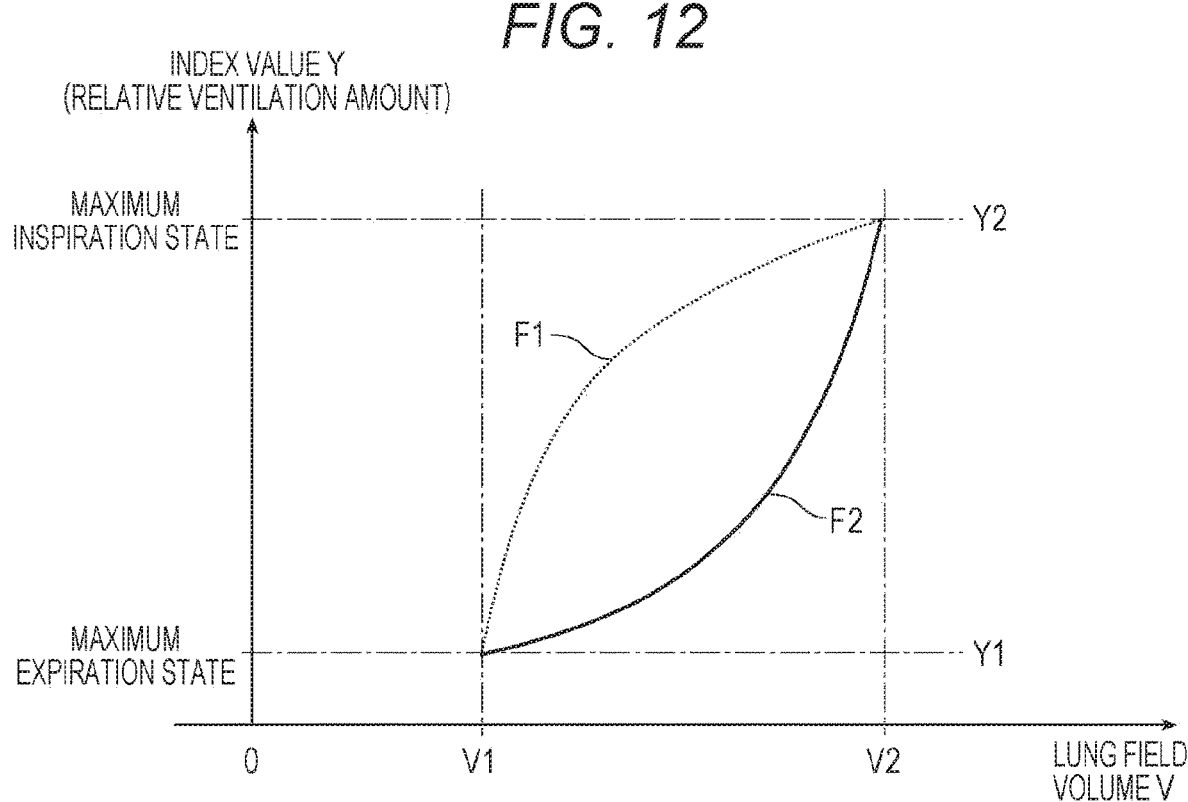
FIG. 12 is a diagram illustrating a relationship between the lung field volume and the index value (relative ventilation amount) representing the ventilation state.
Figure 13:
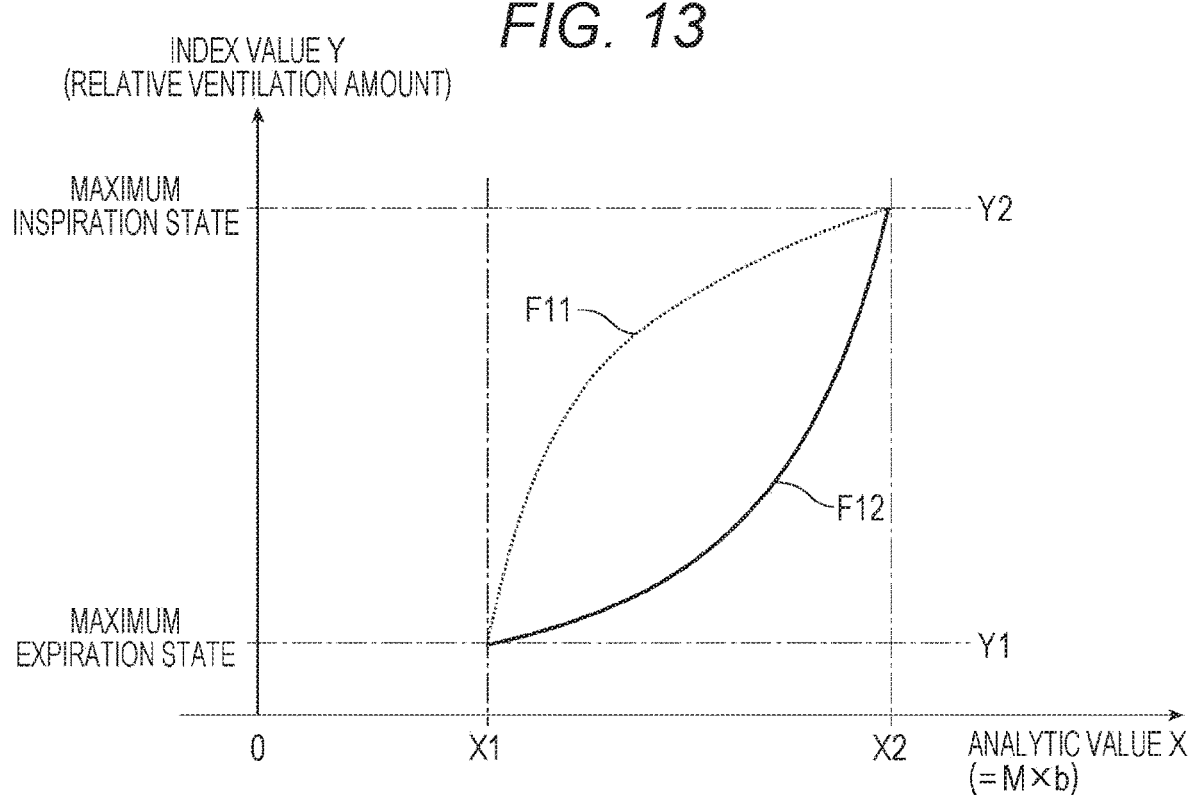
FIG. 13 is a diagram illustrating a function for calculating the index value (relative ventilation amount) representing the ventilation state on the basis of the analytic value (M×b)

Although the analytic value X obtained in the above-described (Formula 1) is not an actual measurement value of the lung field volume, the analytic value X is considered to be in a linear relationship with a lung field volume V as illustrated in FIG. 11. The change in the ventilation amount, however, is delayed compared with the change in the lung field volume, as illustrated with FIGS. 9 and 10. Accordingly, in a case where the index value Y representing the ventilation state is defined as the relative ventilation amount, the relationship between the lung field volume V and the index value Y is represented by an upward curved non-linear function F1 in the expiratory phase, and represented by an downward curved non-linear function F2 in the inspiratory phase, as illustrated in FIG. 12. Accordingly, when the horizontal axis represents the analytic value X (=M×b) and the vertical axis represents the index value Y (relative ventilation amount), an upward curved non-linear function F11 is obtained in the expiratory phase, while a downward curved non-linear function F12 is obtained in the inspiratory phase, by combining the cases in FIGS. 11 and 12, as illustrated in FIG. 13. In a similar manner, in a case where the lung field region is divided into a plurality of regions, the relationship between the analytic value X and the index value Y in each of the region is represented by a non-linear function as illustrated in FIG. 13.

Moreover, the lung field volume differs between the upper lung field region and the lower lung field region (volume is larger in the lower lung field than in the upper lung field), leading to a difference in the absolute ventilation amount in substantially proportion to this relationship. Moreover, there is also a difference, in case of the standing position state, in the force applied to the alveoli between the upper lung field region and the lower lung field region due to the gravity, leading to the difference in the degree of delay of the ventilation amount with respect to the volume change depending on the region. Furthermore, while the analytic value X is a value calculated on the basis of the number of pixels in the present embodiment, there might be a case where the analytic value X is a value obtained on the basis of the signal value of the pixel, such as the transmitted X-ray intensity. In this case, since the upper lung field in the standing position is extended by the weight of the alveoli in the whole lung field and causes low alveoli density, leading to a low signal value in an original state. In contrast, the lower lung field has less extension attributed to the weight of the alveoli and causes higher alveoli density, leading to higher signal value in the original state, compared with the upper lung field.

Figure 14:
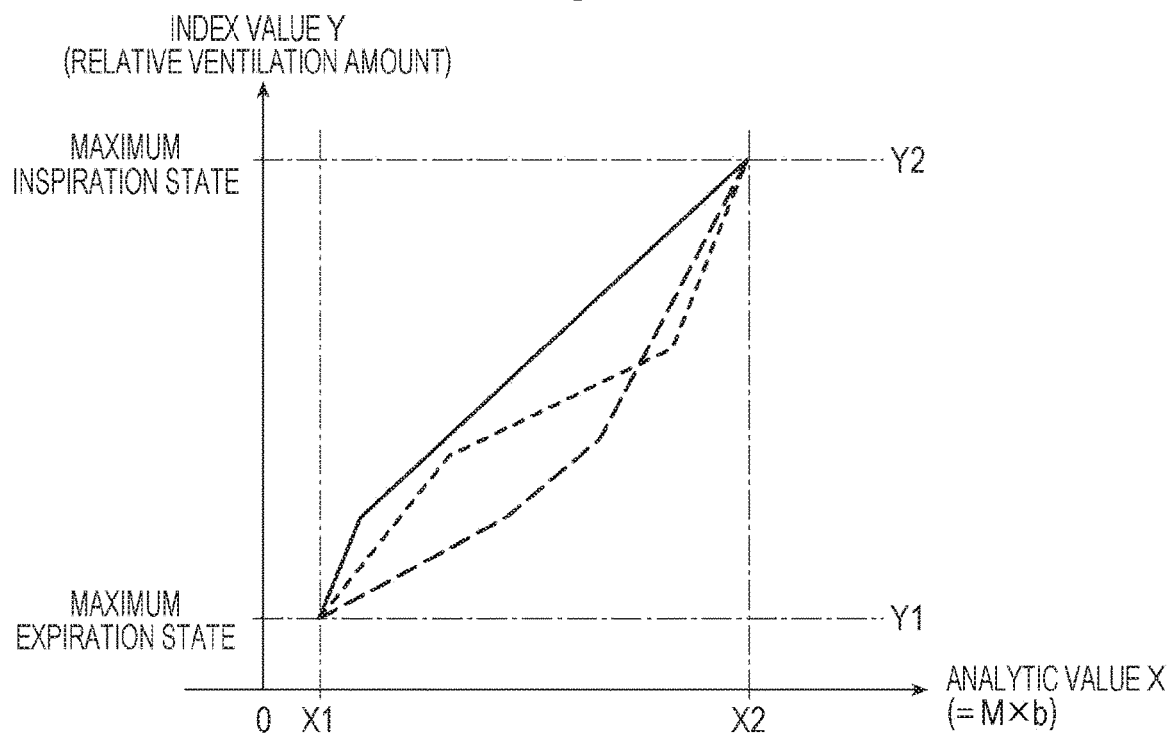
FIG. 14 is a diagram illustrating another exemplary shape of the function.

Correspondingly, in the present embodiment, the storage unit 44 stores various non-linear functions different from each other in accordance with each of the regions, as illustrated in FIG. 13. The non-linear function may be a function approximated by a plurality of lines with different inclination, as illustrated in FIG. 14.

Note that, by fixing a changing range of the index value Y irrespective of the region within the lung field, it would be possible to determine the ventilation state with a same standard for any region within the lung field. Accordingly, in order to fix the range of change in the index value Y irrespective of the region within the lung field, it would be preferable to use a function having a large absolute value R of the inclination as the function corresponding to a region A of the upper lung field having a smaller change in the analytic value X caused by ventilation and to use a function having a small absolute value R of the inclination as the function corresponding to a region C of the lower lung field having a larger change in the analytic value X caused by ventilation. The absolute value R of inclination of the function corresponds to a ratio ($|Y2-Y1|/|X2-X1|$). The ratio ($|Y2-Y1|/|X2-X1|$) is a ratio of a difference $|Y2-Y1|$ between the index value Y1 representing the ventilation state at the maximum expiration level, and the index value Y2 representing the ventilation state at the maximum inspiration level, to a difference $|X2-X1|$ between the analytic value X1 at the maximum expiration level, and the analytic value X2 at the maximum inspiration level.

Figure 15A:
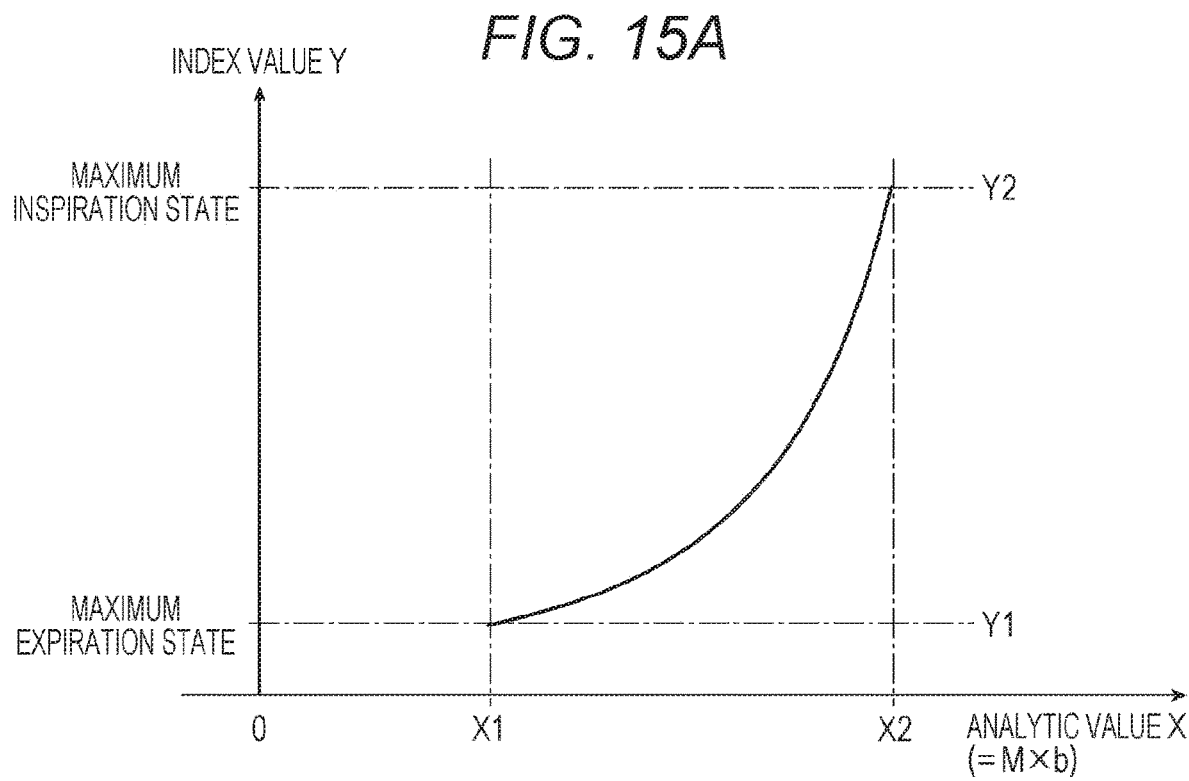
FIG. 15A is a diagram illustrating an exemplary function in an inspiratory phase.
Figure 15B:
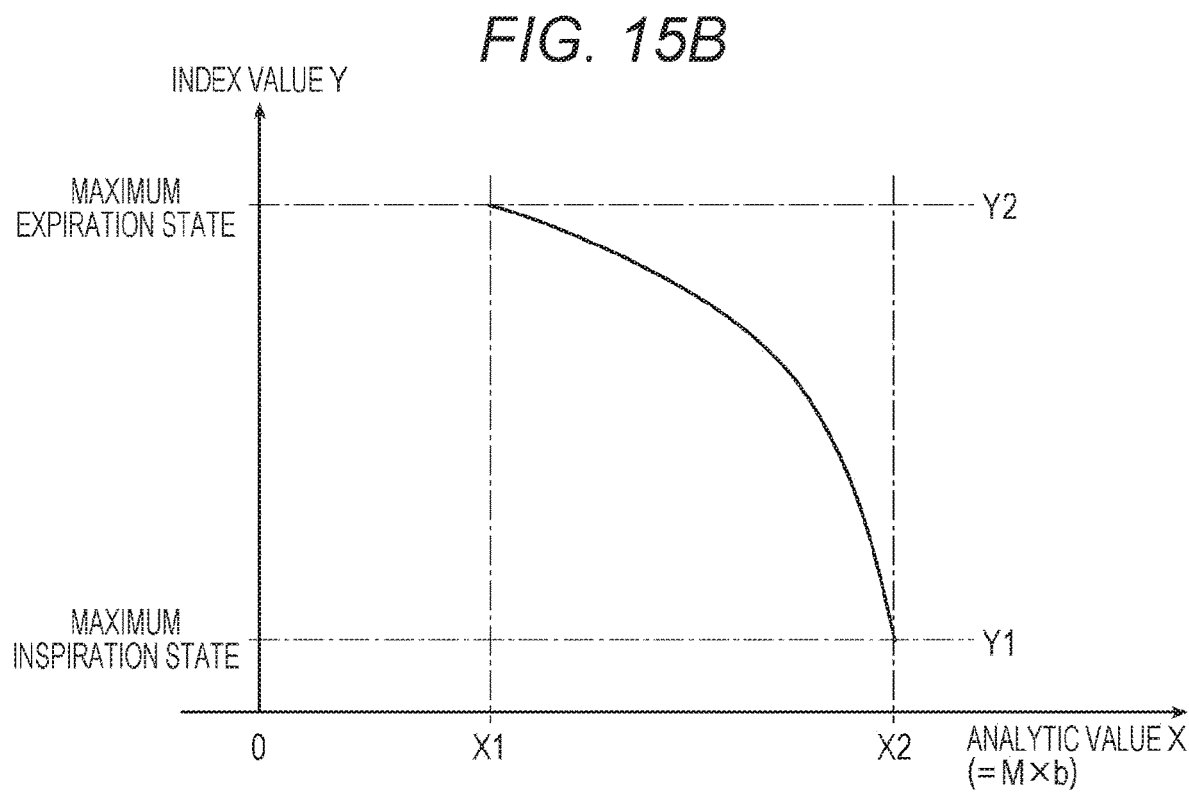
FIG. 15B is a diagram illustrating an exemplary function in an expiratory phase.

Alternatively, it is also allowable to apply a mutually different function to each of the expiratory phase and the inspiratory phase, corresponding to each of the regions. For example, as illustrated in FIGS. 15A and 15B, an increase/decrease of the index value Y with respect to the increase/decrease of the analytic value X may be reversed, between the expiratory phase and the inspiratory phase. FIG. 15A illustrates an exemplary function of the inspiratory phase and FIG. 15B illustrates an exemplary function of the expiratory phase. As illustrated in FIGS. 15A and 15B, with use of the functions in which the increase/decrease of the index value Y with respect to the increase/decrease of the analytic value X is reversed, between the expiratory phase and the inspiratory phase, it is possible to calculate, regarding the inspiratory phase, the index value Y representing the ventilation state (that is, inspiration amount) in each of the time phases for a case where the index value Y representing the ventilation state at the maximum expiration level is defined as a standard (e.g. zero). Together with this, regarding the expiratory phase, it is possible to calculate, regarding the expiratory phase, the index value Y representing the ventilation state (that is, expiration amount) in each of the time phases for a case where the index value Y representing the ventilation state at the maximum inspiration level is defined as a standard (e.g. zero).

Next, the image analysis unit 47 calculates the index value Y representing the ventilation state from the analytic value X, for each of the regions of each of the dynamic images, using the function obtained by the information acquisition unit 48 (step S15).

Subsequently, the image analysis unit 47 attaches, to the dynamic image, the information on the index value Y representing the ventilation state individually calculated for each of the regions of each of the dynamic images in the inspiratory phase and the expiratory phase (step S16). Thereafter, the dynamic image in individual time phases, to which the information on the index value Y representing the ventilation state of each of the regions has been attached, is transmitted to the server 50 via the communication unit 45.

The server 50 forms a database from the dynamic image in each of the time phases together with the attachment information and stores the database in the memory. When a request is received from the diagnosis console 30, the server 50 transmits a group of dynamic images of the related patient according to the request.

Returning to FIG. 4, the diagnosis console 30 displays the dynamic image in each of the time phases obtained from the server 50, on the display unit 34 under the display control of the control unit 31 (step S4). At this time, the control unit 31 displays each of the dynamic images as a moving image by continuously switching the dynamic images in accordance with the time phase. This enables the physician to grasp dynamic changes regarding the lung respiratory motion.

Note that when the signal value and the analytic value X are displayed on the display apparatus, display is typically performed in simple X-ray radiography diagnosis, such that the lower the transmitted X-ray intensity, the higher the luminance (brighter), while higher the transmitted X-ray intensity, the lower the luminance (darker). Alternatively, it is allowable to display in a bright/dark reversed manner, or switch the way of display of both in accordance with the usage and preference.

Next, the control unit 31 displays information of the index value Y representing the ventilation state on the display unit 34 on the basis of the information attached on the displayed dynamic image (step S5: control unit).

Figures 16, 17:
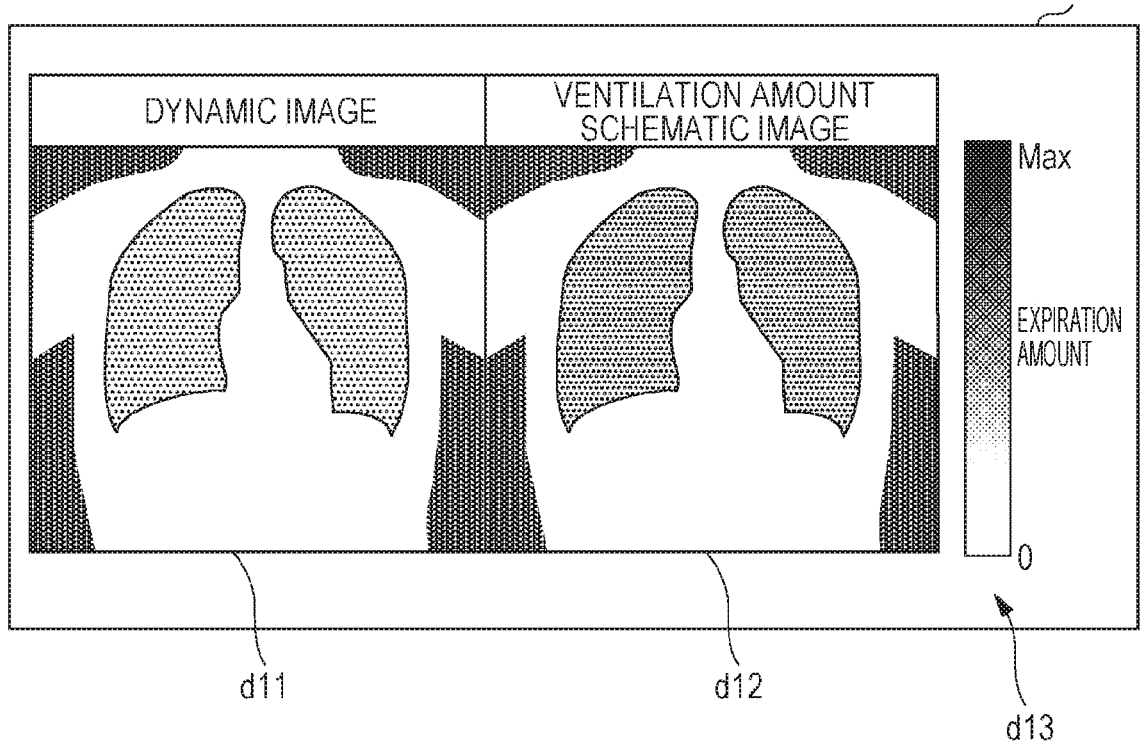
FIG. 16 is a diagram illustrating an exemplary display of the index value representing the dynamic image and the ventilation state.
FIG. 17 is a diagram illustrating an exemplary user interface screen for associating the index value representing the ventilation state with a display color.

FIG. 16 illustrates an exemplary display of the dynamic image and an exemplary display of the index value Y representing the ventilation state.

A display screen d1 illustrated in FIG. 16 displays a display region d11 for the dynamic image and a display region d12 for the index value Y representing the ventilation state. In the display region d11, the control unit 31 displays each of the dynamic images by continuously switching the images in accordance with the time phase. Meanwhile, in the display region d12 of the index value Y representing the ventilation state, the control unit 31 generates and displays a schematic image illustrating the index value Y representing the ventilation state, calculated on each of the dynamic images. The schematic image illustrating the index value Y representing the ventilation state is a representation of the index value Y representing the ventilation state for each of the divided regions in the color that corresponds to the index value Y, on each of the dynamic images. An indicator d13 that indicates the correspondence between the color density and the ventilation amount is displayed on a position adjacent to the display region d12. On the indicator d13, zero is displayed at the lower limit portion and a Max value is displayed at the upper limit portion, of the relative ventilation amount as the index value Y. Furthermore, it is also allowable to cause the control unit 31 to display the index value Y representing the ventilation state for each of the regions, calculated for each of the dynamic images using numerical values.

The color corresponding to the index value Y representing the ventilation state on the schematic image may be represented by gradation of a single hue such as white, red, blue, and green, or may be represented by colors with a plurality of difference hues. For example, 0 to 0.2 may be displayed in blue, 0.2 to 0.4 in green, 0.4 to 0.6 in yellow, 0.6 to 0.8 in orange, and 0.8 to 1.0 in red, within the relative ventilation amount (0 to 1). Regarding association between the index value Y representing the ventilation state and the color for display (gradation and hue), it would be preferable to configure so as to display a user interface screen d2 as illustrated in FIG. 17 and to enable the user to perform selection as desired.

Figure 18:
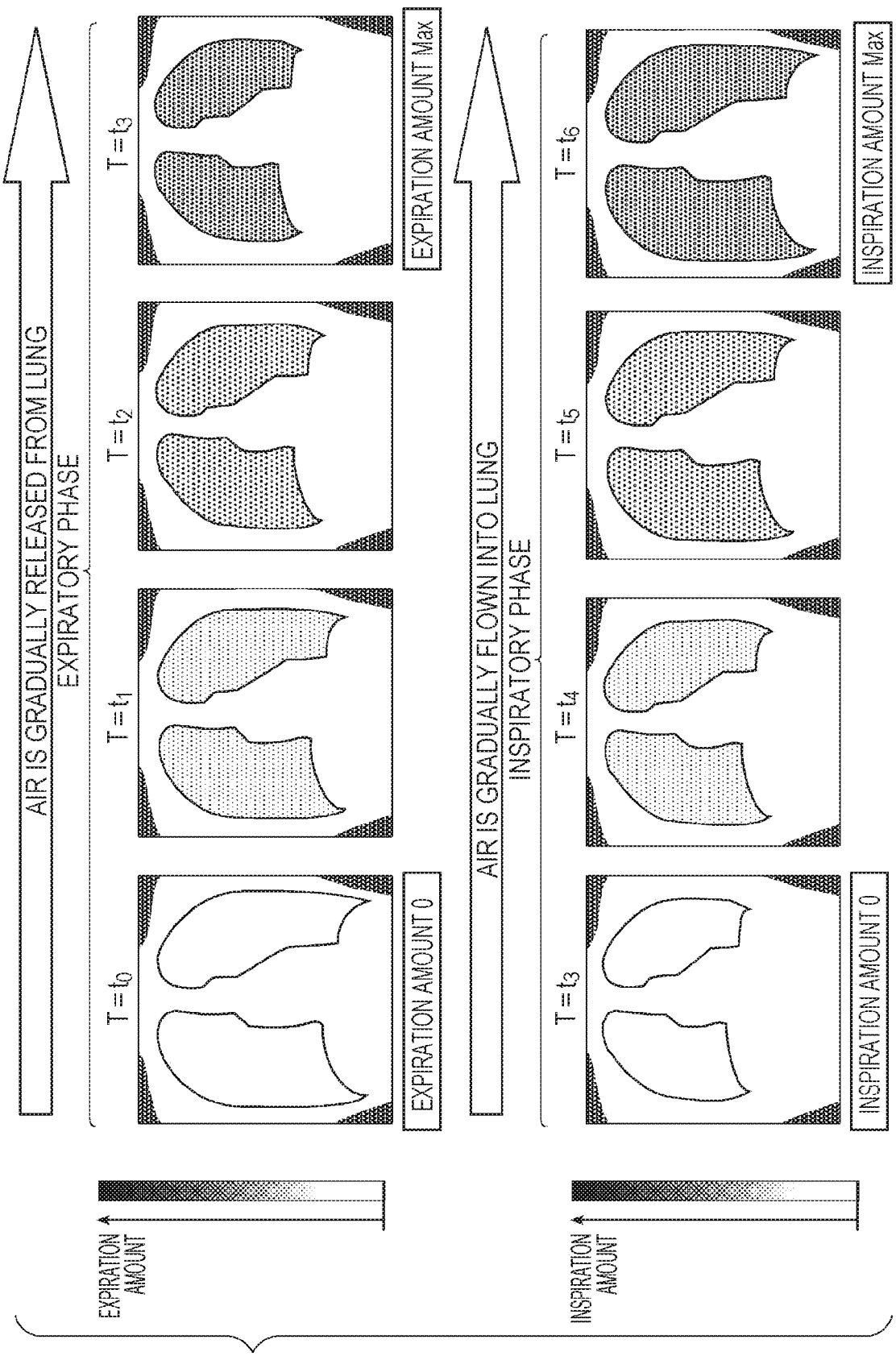
FIG. 18 is a schematic image of the index value representing the ventilation state.

FIG. 18 is an exemplary schematic image of the index value Y representing the ventilation state. FIG. 18 illustrates the index value Y calculated using a function having a difference in the increase/decrease in the index value Y with respect to the increase/decrease in the analytic value X, between the expiratory phase and the inspiratory phase, illustrated in FIGS. 15A and 15B. The upper example illustrates the case of the relative ventilation amount (expiration amount) of the expiratory phase and the lower example illustrates the case of the relative ventilation amount (inspiration amount) of the inspiration phase. FIG. 18 illustrates an exemplary schematic image illustrating the index value Y representing the ventilation state of a healthy subject.

As illustrated in an upper example in FIG. 18, in the case of the expiratory phase, each of the regions on the dynamic image with each of the time phase being T=$t_0$, $t_1$, $t_2$, and $t_3$, is represented in a color that corresponds to the expiration amount in each of the regions on the basis of the expiration amount of zero on the dynamic image at the maximum inspiration level (time phase T=$t_0$). This enables visualized illustration of the change in the expiration amount for each of the regions on the basis of the expiration amount at the maximum inspiration level as a standard. Note that it would be sufficient to subtract Y1 from the index value Y in order to set the expiration amount of the dynamic image at the maximum inspiration level, to zero.

Similar description applies also to the case of the inspiratory phase. As illustrated in a lower example in FIG. 18, in the case of the inspiratory phase, each of the regions on the dynamic image with each of the time phase being T=$t_3$, $t_4$, $t_5$, and $t_6$, is represented in a color that corresponds to the inspiration amount in each of the regions on the basis of the inspiration amount of zero on the dynamic image at the maximum expiration level (time phase T=$t_3$). This enables visualized illustration of the change in the inspiration amount for each of the regions on the basis of the inspiration amount at the maximum expiration level as a standard. Note that it would be sufficient to subtract Y1 from the index value Y in order to set the inspiration amount of the dynamic image at the maximum expiration level, to zero.

The present embodiment calculates the index value Y from the analytic value X using a non-linear function taking into consideration the delay in the change of the ventilation amount with respect to the change in the lung field volume along with respiration. Accordingly, it is possible to provide more accurate information on the ventilation state of the lung field compared with the known art. Moreover, different functions are used corresponding to the regions of the lung field, and therefore, in a case where photography is performed in a standing position, it is possible to calculate the index value Y in consideration of the difference in the degree of delay of the change in the ventilation amount with respect to the change in the volume of the upper lung field region and the lower lung field region due to the gravity. Accordingly, it is possible to provide more accurate information on the ventilation state. Furthermore, since the upper lung field and the lower lung field naturally have different lung field volumes, the absolute ventilation amount differs depending on the region of the lung field. In this, since different functions are used corresponding to the regions, it is possible to calculate the index value Y in consideration of the difference in the absolute ventilation amount between the regions, and to provide more accurate information on the ventilation state.

The control unit 31 displays the schematic image in which each of the regions is represented by the color that corresponds to the index value Y representing the ventilation state in each of the dynamic images, on the display region d12 while continuously switching the schematic image in accordance with the time phases. With the change in the color on the schematic image, the physician can visually grasp a change over time in the index value Y representing the ventilation state.

Note that switching display is performed in accordance with the time phase of the original dynamic image in the display region d11. By linking the display of the original dynamic image and a dynamic state, the user including the physician can use the information on the index value Y representing the ventilation state as a reference, while observing the original dynamic image.

Second Embodiment

Next, a second embodiment of the present invention will be described.

The second embodiment will describe an exemplary case of calculating a representative value of the signal value (transmitted X-ray intensity) within the region obtained by dividing the lung field region, for example, the mean, median, and mode values, as the analytic value X, and obtaining the index value Y (relative ventilation amount) using the function stored in the storage unit 44.

In the second embodiment, the storage unit 44 of the image processing apparatus 40 stores different functions that correspond to each of the regions for calculating the relative ventilation amount as the index value Y from the representative value of transmitted X-ray intensity as the analytic value X, and the index value Y is calculated from the analytic value X on the basis of the function stored in the storage unit 44 in step S15 in FIG. 5. Other configurations and operation of the dynamic analysis system 1 are similar to the description of the first embodiment, and thus, description will be omitted, and hereinafter, the function stored in the storage unit 44 will be described.

When respiration (ventilation) is performed, the diaphragm moves in a vertical direction (y-direction) and the outer thorax moves in a substantially lateral direction (x-direction). That is, ventilation (on a healthy subject) produces a change in a lung field area in the x- and y-directions. Accordingly, the relationship between the ventilation state, the lung field area, and the transmitted X-ray intensity with a primitive cubic model will be studied with reference to FIG. 19.

Figure 19:
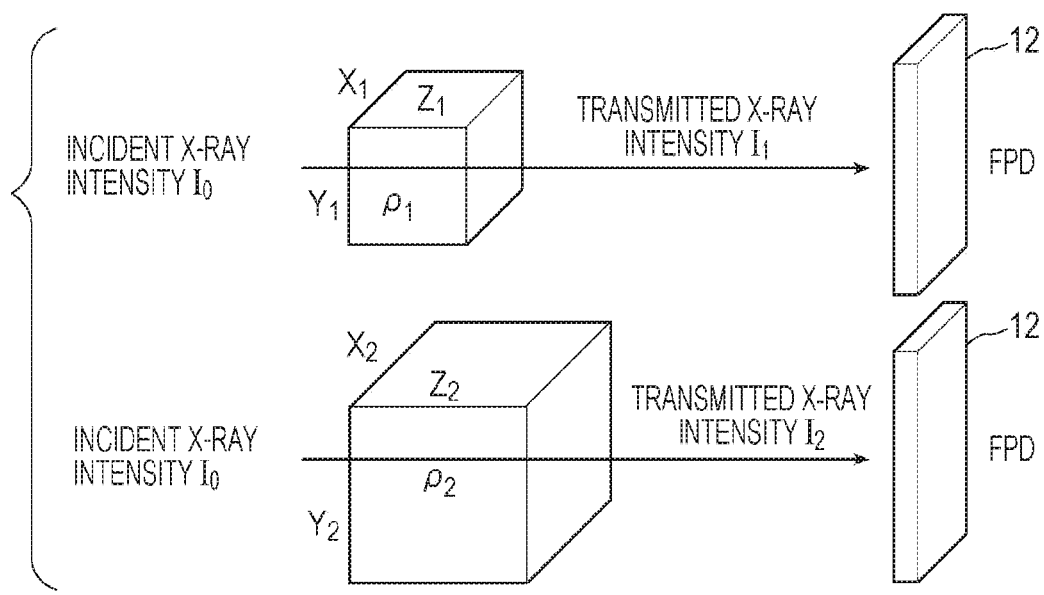
FIG. 19 is a diagram for illustrating a relationship between the ventilation state, the area of the lung field, and the transmitted X-ray intensity, with a primitive cubic model.

First, it is assumed, as illustrated in FIG. 19, that a predetermined cube (volume: x1×y1×z1) is cut out from the lung field in an inspiration state. Since the alveoli expands by the inspiration, the volume of the cube having the same number of alveoli expands from (x1×y1×z1) to (x2×y2×z2). Herein, ρ1 and ρ2 illustrated in FIG. 19 represents density [g/cm³] of the alveoli per unit volume. Since the mass of alveoli before and after expansion of the cube having the same number of alveoli is the same, the following (Formula 2) is satisfied.

[Mathematical Expression 1]

$$\rho_1 \times x_1 y_1 z_1 = \rho_2 \times x_2 y_2 z_2 \quad \text{(Formula 2)}$$

Accordingly, $$\rho_2 = \rho_1 \times \frac{x_1 y_1 z_1}{x_2 y_2 z_2}$$

When the linear mass absorption coefficient of the alveoli is p, each of transmitted X-ray intensity I1 and I2 can be represented by the following (Formula 3) and (Formula 4).

[Mathematical Expression 2]

$$I_1 = I_0 \exp[-\mu \times \rho_1 \times z_1] \quad \text{(Formula 3)}$$

[Mathematical Expression 3]

$$I_2 = I_0 \exp\left[-\mu \times \rho_1 \times \frac{x_1 y_1 z_1}{x_2 y_2 z_2} z_2\right] = \quad \text{(Formula 4)}$$

$$I_0 \exp\left[-\mu \times \rho_1 \times \frac{x_1 y_1}{x_2 y_2} z_1\right] \left(\rho_2 = \rho_1 \times \frac{x_1 y_1 z_1}{x_2 y_2 z_2}\right)$$

When x1 and y1 are the areas in the standard state (for example, maximum expiration state), and when I2 is replaced with the transmitted X-ray intensity in a certain respiratory state and x2 and y2 are replaced with the area xy in a certain respiratory state, the result would be as follow.

[Mathematical Expression 4]

$$I = I_0 \exp\left[-\mu \times \rho_1 \times \frac{x_1 y_1}{xy} z_1\right] \quad \text{(Formula 5)}$$

When (Formula 5) is solved to obtain xy,

[Mathematical Expression 5]

$$xy = \mu \times \rho_1 \times \frac{x_1 y_1}{\ln(I_0) - \ln(I)} z_1 \quad \text{(Formula 6)}$$

$$\left(\begin{array}{c} ln \text{ is natural logarithm} \\ I < I_0 \end{array}\right)$$

When the cube is assumed to contract isotropically, a thickness direction z is considered to contract in a same ratio as the ratio of x and y. In this case, when the area xy is N, the length of one side is N^(1/2), and the volume is the cube thereof, being N^(3/2). That is as illustrated in (Formula 7), when the cube is assumed to contract isotropically, the volume V of the cube is the 3/2 power of xy.

[Mathematical Expression 6]

$$V = (xy)^{3/2} \quad \text{(Formula 7)}$$

Substituting (Formula 6) into (Formula 7) gives:

[Mathematical Expression 7]

$$V = \left(\mu \times \rho_1 \times \frac{x_1 y_1}{\ln(I_0) - \ln(I)} z_1\right)^{3/2} \quad \text{(Formula 8)}$$

Figure 20:
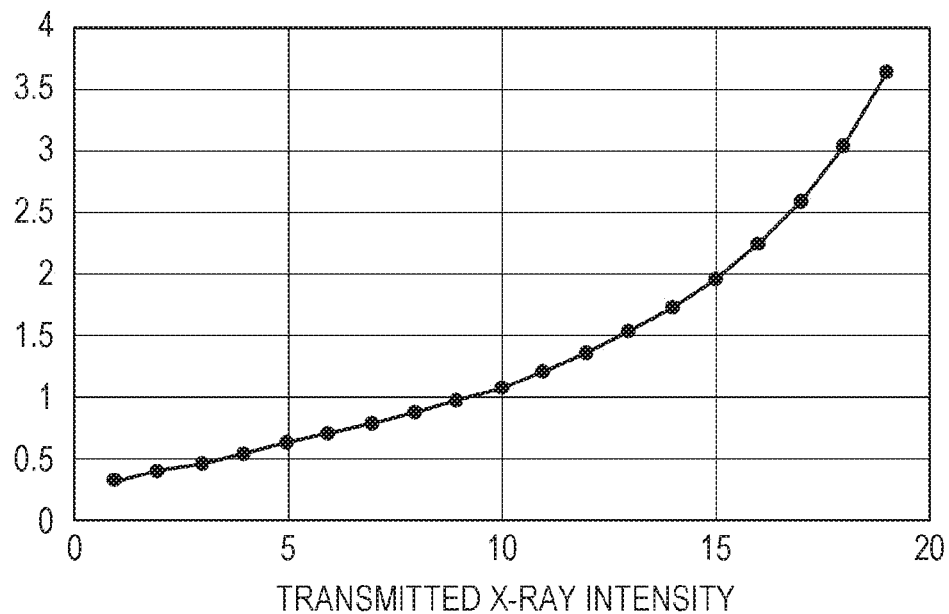
FIG. 20 is a graph illustrating a relationship between the transmitted X-ray intensity and the volume of the lung field.

From (Formula 8), the relationship between the transmitted X-ray intensity I and the volume V is a non-linear relationship, as illustrated in FIG. 20.

Figure 21:
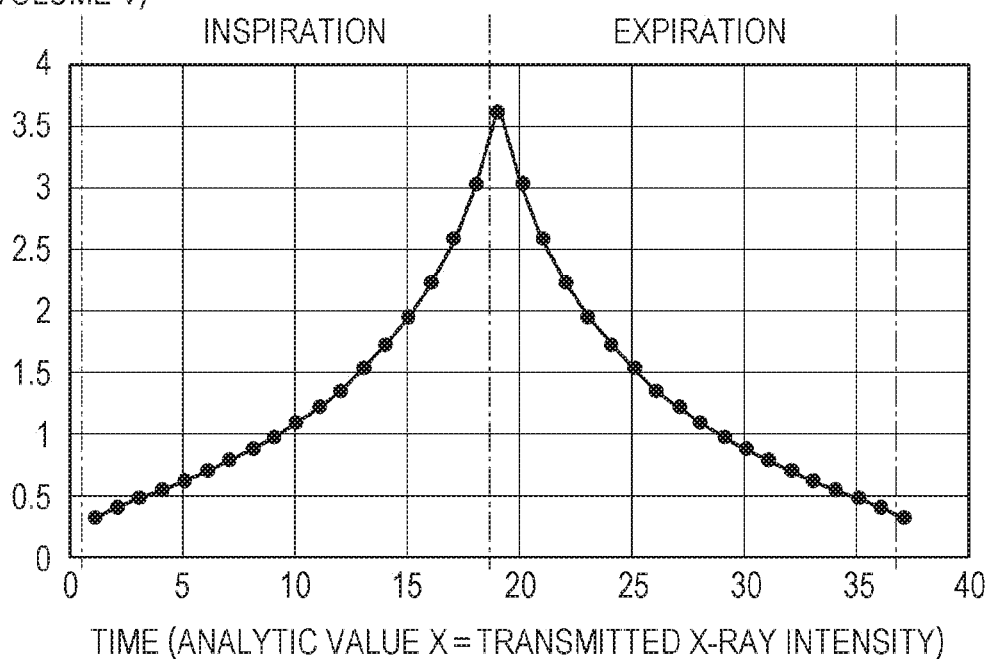
FIG. 21 is a graph plotting the volume obtained from FIG. 20, that corresponds to the transmitted X-ray intensity obtained from the dynamic image in each of time from start of photographing.

Note that the transmitted X-ray intensity in the lung field region in the plurality of time phases changes with the time phase. Accordingly, when the volume that corresponds to the transmitted X-ray intensity obtained from the dynamic image in each of the times is obtained from FIG. 20 and plotted on a graph having the horizontal axis defined as the time and the vertical axis defined as the volume V, the relationship between the volume V and the time (analytic value X=transmitted X-ray intensity) is as illustrated in FIG. 21.

Note that the lung field volume V and the ventilation amount are substantially proportional to each other. Accordingly, in a case where the change in the ventilation amount is not delayed with respect to the change in the lung field volume, the relationship between the relative ventilation amount and the time (and analytic value X=transmitted X-ray intensity, corresponding to the time) also has a non-linear relationship as illustrated in FIG. 21.

Figure 22:
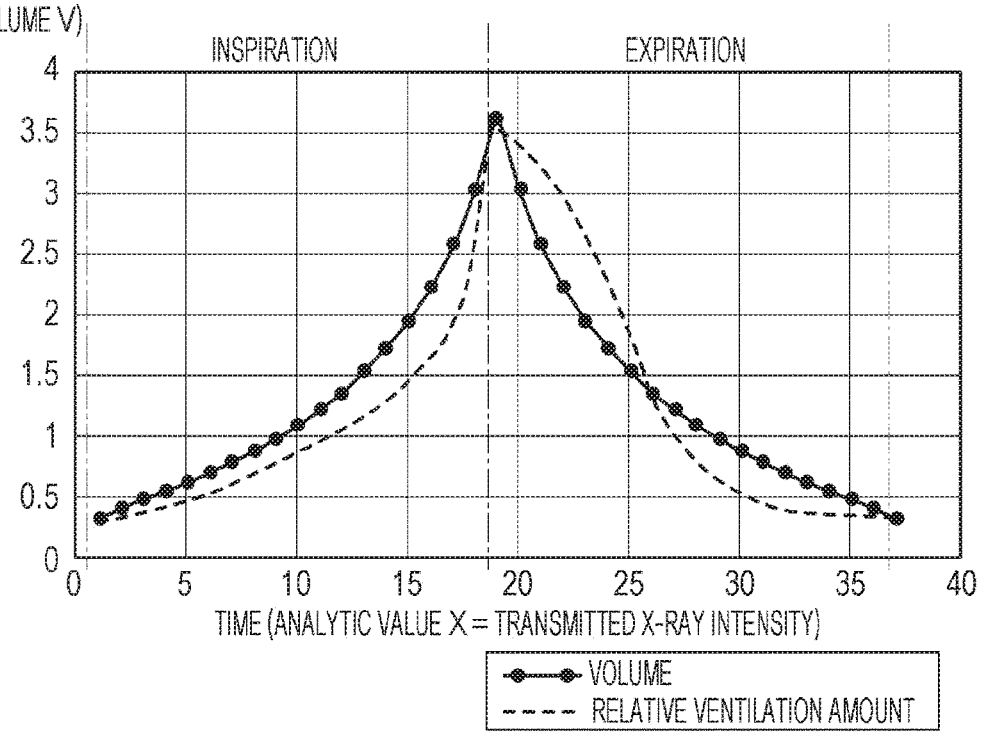
FIG. 22 is a graph illustrating the relative ventilation amount that corresponds to the transmitted X-ray intensity obtained from the dynamic image in each of time from start of photographing.

Actually, as described in the first embodiment, the change in the ventilation amount is delayed with respect to the change in the lung field volume V, and thus, the temporal change of the relative ventilation amount is as illustrated in dotted lines in FIG. 22. The relationship between the analytic value X (transmitted X-ray intensity) and the index value Y (relative ventilation amount) is obtained on the basis of FIG. 22. This results in a non-linear function having a section including an upward curve and a downward curve for the expiratory phase, and a downward curved non-linear function for the inspiratory phase, as illustrated in FIG. 23.

Figure 23:
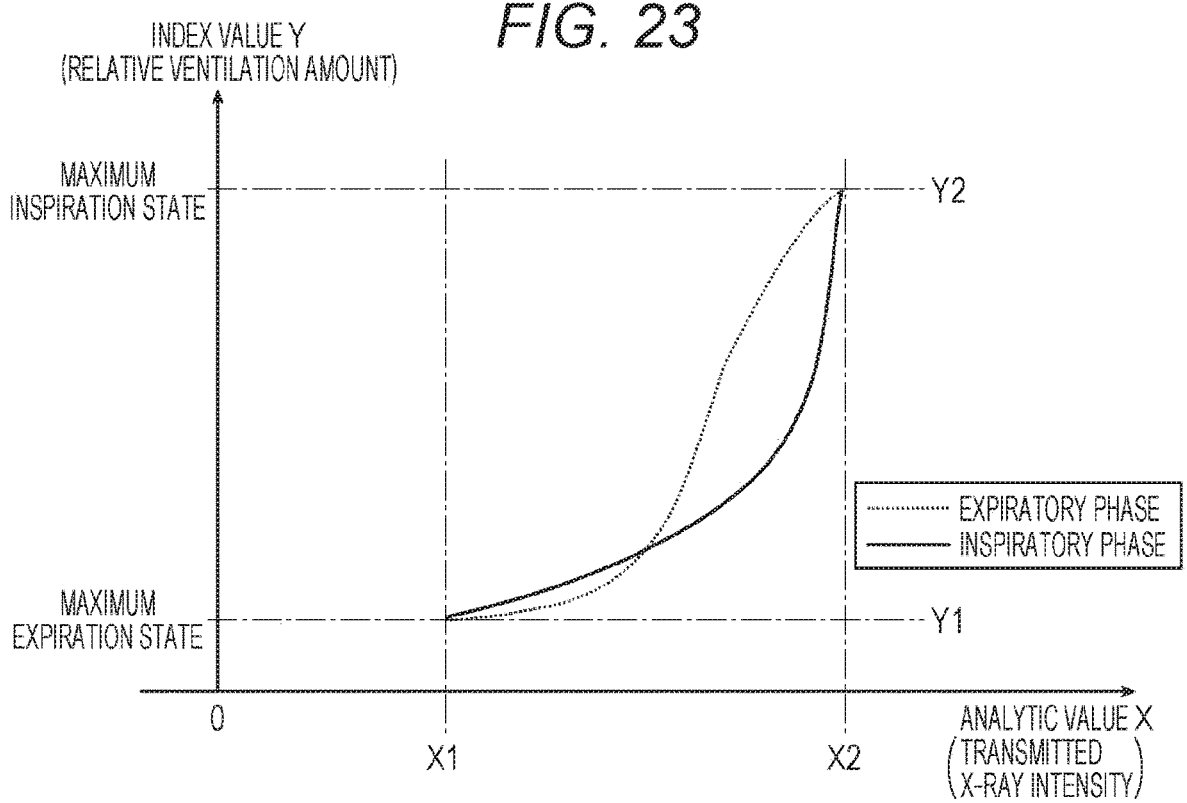
FIG. 23 is a diagram illustrating an exemplary function used in calculation of the index value representing the ventilation state, from the analytic value in a second embodiment.

Accordingly, in the present embodiment, the storage unit 44 stores a non-linear function as illustrated in FIG. 23, corresponding to each of the regions. Note that, as described in the first embodiment, the non-linear function stored in the storage unit 44 may be the function approximated by a plurality of lines with different inclinations (refer to FIG. 13). Moreover, it is allowable to use a function in which the increase/decrease of the index value Y is reversed with respect to the increase/decrease of the analytic value X, between the expiratory phase and the inspiratory phase (refer to FIGS. 15A and 15B).

The present embodiment calculates the index value Y from the analytic value X using a non-linear function taking into consideration the relationship between the transmitted X-ray intensity and the relative ventilation amount. Accordingly, it is possible to provide more accurate information on the ventilation state of the lung field compared with the known art. Moreover, since different functions are used corresponding to the region of the lung field, in a case where photography is performed in a standing position, for example, it is possible to calculate the index value Y in consideration of the difference in the degree of delay in change in the ventilation amount with respect to the change in the volume of the upper lung field region and the lower lung field region due to the gravity. Accordingly, it is possible to provide more accurate information on the ventilation state. Moreover, since the upper lung field and the lower lung field have different original lung field volumes, the absolute ventilation amount differs depending on the region of the lung field. In this, since different functions are used corresponding to the regions, it is possible to calculate the index value Y in consideration of the difference in the absolute ventilation amount between the regions, and to provide more accurate information on the ventilation state. Furthermore, different functions are used corresponding to the regions of the lung field, and thus, in a case where photography is performed in a standing position, for example, it is possible to calculate the index value Y in consideration of the difference in the signal values due to the difference in alveoli density between the upper lung field region and the lower lung field region due to the weight of the alveoli. Accordingly, it is possible to provide more accurate information on the ventilation state.

Hereinabove, the first and second embodiments of the present invention have been described. The above-described embodiments, however, are preferable example of the present invention and the configuration is not limited to this.

For example, the embodiment above describes an exemplary case as the best mode of the present invention where the lung field region is divided and the index value Y representing the ventilation state is calculated from the analytic value X using different functions for each of the divided functions. The configuration, however, is not limited to this. For example, the present invention is applicable to a case where the index value Y is calculated from the analytic value X using a single function toward the entire lung field region without dividing the lung field region. Moreover, the present invention is applicable to a case where the index value Y is calculated using a same function for each of the regions, in a case where the lung field region is divided and the index value Y is calculated from the analytic value X in each of the divided regions.

Moreover, what is described is a configuration in which the index value Y representing the ventilation state is displayed on the diagnosis console 30. The index value Y, however, may be displayed on the photography console 20 or other apparatuses (diagnosis PC, or the like). Moreover, the described configuration is a case where the image processing apparatus 40 that performs image processing is provided and the image processing apparatus 40 calculates the index value Y representing the ventilation state. Alternatively, it is also allowable to perform calculation by installing a program for calculating the index value Y representing the ventilation state, on the diagnosis console 30 and other apparatuses.

Moreover, as a computer-readable medium for storing the program related to the above-described processing, it is possible to apply portable type medium such as a DVD, other than a memory such as a ROM. Moreover, as a medium that provide program data via a network, carrier waves (carrier) is also applicable.

In addition, detailed configurations and detailed operation of each of the apparatuses configuring the dynamic analysis system can be appropriately modified without departing from the spirit and scope of the present invention.

Although the present invention has been described and illustrated in detail, it is clearly understood that the same is by way of illustrated and example only and is not to be taken by way of limitation, the scope of the present invention being interpreted by terms of the appended claims.

What is claimed is:

1. A radiographic dynamic analysis system comprising:
    an analytic value calculation unit configured to calculate an analytic value in a plurality of time phases on the basis of a radiographic dynamic image in the plurality of time phases obtained by performing radiographic dynamic photography on the chest of a subject, wherein the analytic value is one of transmitted X-ray intensity and a value calculated using the transmitted X-ray intensity;
    a ventilation state calculation unit configured to calculate, using a non-linear function that is predetermined, an index value representing a ventilation state of a lung field from the analytic value in the plurality of time phases, wherein the ventilation state represented by the index value is an air amount within the lung field or a change amount of the air within the lung field, wherein the non-linear function used in an inspiratory phase is a function having a downward curve at least in a portion of the region and the non-linear function used in an expiratory phase is a function having an upward curve at least in a portion of the region;
    a display unit; and
    a control unit configured to display information indicating the index value calculated on the plurality of time phases, on the display unit.

2. The radiographic dynamic analysis system according to claim 1,
    wherein the analytic value is one of transmitted X-ray intensity and a value calculated using the transmitted X-ray intensity.

3. The radiographic dynamic analysis system according to claim 1,
    wherein the index value represents the air amount within the lung field.

4. The radiographic dynamic analysis system according to claim 1,
    wherein the ventilation state calculation unit calculates the index value from the analytic value using different functions for each of an expiratory phase and an inspiratory phase.

5. The radiographic dynamic analysis system according to claim 4,
wherein the ventilation state calculation unit uses a function in which an increase/decrease of the index value is reversed with respect to the increase/decrease of the analytic value, between the expiratory phase and the inspiratory phase.

6. The radiographic dynamic analysis system according to claim 1, the non-linear function used in the expiratory phase includes a region having a downward curve and a region having the upward curve.

7. The radiographic dynamic analysis system according to claim 1, further comprising:
a storage unit configured to store the non-linear function; and
an information acquisition unit configured to obtain the non-linear function stored in the storage unit,
wherein the ventilation state calculation unit calculates the index value representing the ventilation state from the analytic value using the non-linear function obtained by the information acquisition unit.

8. The radiographic dynamic analysis system according to claim 1,
wherein the analytic value calculation unit divides a lung field region included in the dynamic image in the plurality of time phases, into a plurality of regions, and calculates an analytic value of each of the divided regions in the plurality of time phases,
the ventilation state calculation unit calculates an index value representing a ventilation state of each of the regions from the analytic value of each of the regions in the plurality of time phases, and
the control unit displays the index value calculated for each of the regions in the plurality of time phases, on the display unit.

9. The radiographic dynamic analysis system according to claim 8,
wherein the ventilation state calculation unit calculates the index value representing the ventilation state of each of the regions from the analytic value of each of the regions, using different functions each of which corresponds to each of the regions.

10. The radiographic dynamic analysis system according to claim 9, further comprising:
a storage unit configured to store different functions each of which corresponds to each of the regions; and
an information acquisition unit configured to obtain the different functions each of which corresponds to each of the regions, from the storage unit,
wherein the ventilation state calculation unit calculates the index value representing the ventilation state of each of the regions using the different functions each of which corresponds to each of the regions obtained by the information acquisition unit.

11. The radiographic dynamic analysis system according to claim 1,
wherein the control unit generates a schematic image with a representation of the index value calculated on each of the dynamic images in the plurality of time phases, and displays the schematic image on the display unit by continuously switching the schematic image in accordance with the time phase.

12. The radiographic dynamic analysis system according to claim 1, further comprising a photography unit configured to generate a dynamic image in a plurality of time phases by performing dynamic photography on the chest of a subject.

13. The radiographic dynamic analysis system according to claim 1, wherein the index value represents the change amount of the air within the lung field.

14. The radiographic dynamic analysis system according to claim 11,
wherein the control unit further displays an indicator that indicates a correspondence between the representation of the index value and the ventilation state.

15. The radiographic dynamic analysis system according to claim 14, wherein the representation of the index value is by a color that corresponds to the index value.

* * * * *